United States Patent [19]

Kikuchi et al.

[11] Patent Number: 4,953,937
[45] Date of Patent: Sep. 4, 1990

[54] ILLUMINATION OPTICAL SYSTEM

[75] Inventors: Akira Kikuchi; Katsuya Ono, both of Tokyo, Japan

[73] Assignee: Olympus Optical Co., Ltd., Tokyo, Japan

[21] Appl. No.: 352,492

[22] Filed: May 16, 1989

[30] Foreign Application Priority Data

May 17, 1988 [JP] Japan .................. 63-118154
Oct. 25, 1988 [JP] Japan .................. 63-267196
Mar. 28, 1989 [JP] Japan .................... 1-73796

[51] Int. Cl.$^5$ ............................................. G02B 6/32
[52] U.S. Cl. .............................. 350/96.18; 350/96.26; 362/335
[58] Field of Search ............... 350/96.18, 432, 96.26, 350/437; 362/331, 335

[56] References Cited

U.S. PATENT DOCUMENTS 4,294,511 10/1981 Yamashita et al. ............... 350/96.18
4,530,578 7/1985 Kato ................................... 350/526
4,536,827 8/1985 Berthold, III et al. ............... 362/32
4,674,844 6/1987 Nishioka et al. ................. 350/432 X
4,683,524 7/1987 Ohta .................................. 362/32 X
4,824,225 4/1989 Nishioka ....................... 350/96.18 X

FOREIGN PATENT DOCUMENTS 62-178207 8/1987 Japan .

Primary Examiner—William L. Sikes
Assistant Examiner—Akm E. Ullah
Attorney, Agent, or Firm—Cushman, Darby & Cushman

[57] ABSTRACT

An illumination optical system consisting of a small number of lens components and having a very uniform light distribution characteristic wherein a light source having a two-dimensional extent, a positive lens system so arranged as to locate the front focal point thereof in the vicinity of the light source and having at least one aspherical surface, and a surface to be illuminated are arranged.

38 Claims, 22 Drawing Sheets

4,953,937

ILLUMINATION OPTICAL SYSTEM

BACKGROUND OF THE INVENTION (a) Field of the Invention

The present invention relates to an illumination optical system having a very uniform light distribution characteristic to be used for illuminating a surface with light emitted from a light source of a certain size having a two-dimensional extent across the optical axis, and more specifically an illumination optical system suited for use with non-flexible endoscopes, fiber scopes, video endoscope and so on.

(b) Description of the Prior Art

In a case where rays are led from a light source to a desired location by using a light guide composed of an optical fiber bundle, the rays incident on the light guide at large angles with regard to the axis of the light guide, out of all the rays incident on the light guide, are remarkably attenuated as compared with the rays in parallel to the axis of the light guide while passing through the light guide. Accordingly, out of the rays emerging from the light guide, the rays emerging from the light guide at large angles with regard to the axis of the light guide are low in the intensities thereof as compared with the rays emerging in parallel with the axis of the light guide. When a surface is illuminated directly with these rays, luminance is remarkably different between the center and marginal portion of an illumination field or light distribution characteristic is degraded, thereby producing inconvenience for observation.

In order to correct this defect, attempts have been made to improve the light distribution characteristic by using lenses. As a conventional example to improve such a light distribution characteristic by using lenses, there is known the illumination optical system disclosed by U.S. Pat. No. 4,294,511.

This illumination optical system comprises, as shown in FIG. 1, a non-flexible endoscope equipped with an observation optical system consisting of an objective lens 0, relay lenses $R_1$ and $R_2$, an eyepiece lens E and an object side light guide (hereinafter referred to a second light guide) 2 arranged so as to surround the observation optical system, a light source 4, a light source side light guide (hereinafter referred to as first light guide) 1 and connecting lenses 7, and is so adapted as to lead the light from the light source 4 to the surface of incidence 2a of the object side light guide through the light source light guide 1 and the connecting lenses 7, and illuminate an object through the object side light guide.

The curve A shown in FIG. 2 visualizes a light distribution characteristic determined experimentally on the end surface of emergence of the light source side light guide. When the angle of emergence from the light source side light guide is represented by $\theta$, the curve can be approximated by a quadratic curve B using as a variable $\sin\theta$ given by $I(\sin\theta) = -a\sin^2\theta + b$.

In order to flatten the light distribution characteristic of the light incident on the object side light guide 2, to widen the range of light distribution and further to minimize loss of light in the coupling section, this conventional illumination optical system is so designed as to locate the end surface of emergence of the light source side light guide (the first light guide) in the vicinity of the front focal point of the coupling lens system 7 and locate the end surface of incidence of the object side light guide (the second light guide) in the vicinity of the rear focal point of the coupling lens system.

Since this illumination optical system uses a small number of spherical lenses having strong refractive powers as the coupling lens system, remarkable aberrations are produced at the marginal portion of illumination field.

FIG. 3 shows an enlarged view of the coupling lenses and the surroundings thereof illustrated in FIG. 1. When the focal length of the coupling lens system is represented by f, the angle formed by the ray emerging from each optical fiber of the first light guide with regard to the optical axis is designated by $\theta_1$, the angle formed by the ray incident on the second light guide on the object side with regard to the optical axis is denoted by $\theta_2$, and the distances from optional points on the end surfaces of the respective light guides to the centers thereof are represented by $r_1$ and $r_2$ respectively, the following relations are established in the positional relationship described above:

$$f \sin\theta_1 = r_2$$

$$r_1 = f \sin\theta_2$$

When $\sin\theta$ is taken as the abscissa and intensity I of the illumination light is taken as the ordinate, under the condition to satisfy these formulae, the light distribution characteristic is uniform as illustrated in FIG. 4.

However, when the light distribution characteristic illustrated in FIG. 4 is retraced taking $\theta$ as the abscissa, the light intensity is lowered at the marginal portion and the light distribution characteristic is degraded as shown in FIG. 5, but no practical problem is posed for visual observation or photographing.

In the recent days, however, it is often practised to observe images on a TV monitor with a TV camera connected to the eyepiece of endoscopes. Further, there have been developed a number of video endoscopes equipped with solid-state image sensors built in the distal ends. Furthermore, it is desired to widen field angles of endoscopes.

In cases where images are observed on TV monitors by using the solid-state image sensors as described above, it is almost impossible to obtain sufficient light quantities or sufficient light distribution at the marginal portions of visual fields with the conventional light guide coupling lens system satisfying $r_1 = f \sin\theta_2$ and $r_2 = f \sin\theta_1$ since an increasing number of endoscopes are now used which employ solid-state image sensors having latitude narrower than that of film for a camera and are designed for observation at field angles wider than 100°.

Further, as an illumination optical system designed for the purpose of obtaining favorable light distribution even at the marginal portion of a visual field, there is known the optical system disclosed by Japanese Unexamined Published Patent Application No. 178207/62.

In this illumination optical system, a light source is arranged distantly from an illumination lens. When height of incidence, on the illumination lens, of the light from the light source is represented by h and angle of emergence of the light from the illumination lens is designated by $\theta$, the illumination optical system is so designed as to satisfy the following condition:

$$h \approx k \tan\theta \quad (k: \text{constant})$$

An illumination optical system to be used in endoscopes must provide favorable light distribution and sufficient light intensity within a limited space. However, the illumination optical system disclosed by the above-mentioned Japanese Unexamined Published Patent Application No. 178207/62 can satisfy the above-mentioned condition only within a very narrow range of about 10° of a field angle of the light source, but cannot satisfy the condition for the offaxial ray at a wider field angle of the light source, thereby degrading light distribution. Further, since the light source is arranged distantly from the illumination lens, the lens is enlarged in the diameter thereof and requires a very wide space when the field angle of the light source is widened.

On the other hand, if first light guide 1 and the coupling lenses 7 are freely attachable and detachable to and from the non-flexible endoscope 5 in FIG. 1, an economical advantage will be obtained since a single light source and a single coupling lens system are usable in combination with various types of endoscopes. When a various endoscopes are used selectively with a single light source, however, it is necessary to determine NA (Numerical Aperture) of the light incident on second light guide through the lens, i.e., illumination angle $\theta$ in accordance with the field angle of the endoscope having the widest field angle.

In the recent days where there have been developed endoscopes having wider field angles for coping with broader application and narrower field angles for observation of magnified images at short distances, field angles are largely different depending on types of endoscopes. Accordingly, even the above-described illumination optical system cannot provide light to the marginal portion of visual field when it is used in combination with an endoscope having further wider field angle. When the illumination optical system is combined with an endoscope having a narrow field angle for observing magnified images at short distances, the illumination optical system illuminates even outside the visual field, thereby making illumination light intensity insufficient within the visual field.

As is understood from the foregoing description, the conventional illumination optical system cannot perform effective illumination matched with endoscopes used in combination therewith.

SUMMARY OF THE INVENTION

A main object of the present invention is to provide an illumination optical system having a uniform light distribution characteristic.

Another object of the present invention is to provide an illumination optical system having a uniform light distribution characteristic for wide illumination field angles.

Another object of the present invention is to provide an illumination optical system simple in construction.

According to the present invention the illumination optical system can increase light quantity at the marginal portion of an illumination field by using a lens system in which the rate of the enlargement in an angle of refraction proportional to the increase of the hight of rays becomes lower compared to a lens system satisfying the relationship of f sin $\theta$=r, whereby a light distribution characteristic is improved.

With respect to a case where the illumination optical system of the present invention is applied to an optical system for connecting two light guides in an endoscope, as shown in, for instance, FIG. 7, the illumination optical system comprises a light source having a two-dimensional extent across an optical axis, such as, an end surface of emergence of a first light guide 1, a positive lens system 3, and a surface to be illuminated, such as, an end surface of incidence of a second light guide 2, which end surface of incidence is illuminated by the light source through the positive lens system 3. The end surface of emergence of the first light guide 1 is positioned adjacent the front focal point of the positive lens system 3. The surface to be illuminated is preferably positioned, in the case of the light guide connection optical system, adjacent the rear focal point of the positive lens system 3, although the surface is not exclusively restricted to such position Said lens system is so designed as to satisfy the following condition (1) at least 50% of the sectional area of the effective light flux at the lens system in the range of the condition (2) defined below:

$$\left(\frac{d\theta}{dr_1}\right) \bigg/ \left(\frac{d\theta}{dr_1}\right)_{r_1 = 0} < f / \sqrt{f^2 - r_1^2} \quad (1)$$

$$0 \leq |r_1| \leq |f| \quad (2)$$

wherein the reference symbol $r_1$ represents distance as measured from the optical axis to an optical point on the end surface of emergence of said first light guide, the reference symbol $\theta$ designates angle of incidence on the end surface of incidence of said second light guide formed between the optical axis and the ray emitted from said point in parallel to the optical axis and the reference symbol f denotes focal length of said lens system.

When a relation of f sin $\theta = r_1$ is established in a lens system, we can obtain the following relations:

$$\sin \theta = r_1/f$$

$$\frac{d\theta}{dr_1} = \frac{1}{f} \cdot \frac{1}{\cos \theta} = \frac{1}{f} \cdot \frac{1}{\sqrt{1 - (r_1/f)^2}}, \text{ and}$$

$$\left(\frac{d\theta}{dr_1}\right)_{r_1 = 0} = \frac{1}{f}$$

Hence, by designing the lens system so as to satisfy the condition (1), namely $$\left(\frac{d\theta}{dr_1}\right) \bigg/ \left(\frac{d\theta}{dr_1}\right)_{r_1 = 0} < \frac{1}{\sqrt{f^2 - r_1^2}}$$

it is possible to obtain a smaller ratio of increment of $\theta$ relative to increment of height of ray $r_1$ than that in the example of the conventional illumination optical systems, especially at lens portions having large values of $r_1$. As is understood from the foregoing description, the illumination optical system according to the present invention comprises the lens system satisfying the condition (1) and can have a favorably improved light distribution characteristic.

The above-described effect is obtainable by designing the lens system so as to satisfy the condition (1) not at the entire sectional area of the effective light flux at the lens system but at least at 50% of the sectional area of the effective light flux. In the present invention, as the end surface of emergence of the first light guide is used as a surface-shaped light source, the field angle of the light source is particularly wide. Therefor, when the angle between the optical axis and the light flux which his emitted from said surface light source and incident on the lens system or the angle between the optical axis and the light flux emerging from the lens system is represented by $\phi$, it is desirable to design the lens system to satisfy the condition (1) at an angle $\phi$ not smaller than any angle, as the case may be, between 10° and 15°.

A lens system satisfying the condition (1) can be composed of two or more lens components including a negative lens component and a positive lens component.

In order to compose this lens system of a smaller number of lens components, it is sufficient to use lens components including, at least one positive lens component having an aspherical surface. This aspherical surface has a shape whose curvature is lowered as the lens portions are farther from the optical axis toward the marginal portion and which can be approximated, when the direction along the optical axis is taken as the x axis and the direction perpendicular to the optical axis is taken as the y axis, by the following formula (3):

$$x = \frac{y^2/R}{1 + \sqrt{1 - p(y/R)^2}} + Ey^4 + Fy^6 + Gy^8 + \ldots \quad (3)$$

wherein the reference symbol R represents radius of curvature on the aspherical surface, the reference symbol P represents conic constant, and the reference symbols E, F, G, ... designate the coefficients of aspherical surface of the fourth, sixth, eighth, ... orders, respectively.

In practice, deviation from the design value due to manufacturing error such as flexture of the surface as shown in the dashed line in FIG. 8 is allowable.

In order to minimize the number of the lens components comprised in the lens system, it is sufficient to design so as to satisfy a combination of (4), (5) and (6), a combination of (4), (6), (7), (8), (9), (10) and (11) or a combination of (4), (6), (8), (9), (12), (13) and (14) out of the following conditions (4) through (14) at 50% or more of the area through which the effective light flux is to pass. By designing the lens system so as to satisfy any one of the combinations of these conditions, it is possible to compose the lens system only of one lens component as described later with reference to the embodiments of the present invention.

$$0.2 \leq D/f \leq 3 \quad (4)$$

$$P < 0 \quad (5)$$

$$|\Delta| \leq |x_{max}|/2 \quad (6)$$

$$0 \leq P < 1 \quad (7)$$

$$E \leq 0 \quad (8)$$

$$F \leq 0 \quad (9)$$

$$0 \leq |E \cdot D^{-3}| \leq 1 \quad (10)$$

$$0 \leq |F \cdot D^{-3}| \leq 0.5 \quad (11)$$

$$P \leq 1 \quad (12)$$

$$0.1 \leq |E \cdot D^{-3}| \leq 0.6 \quad (13)$$

$$0 \leq |F \cdot D^{-3}| \leq 0.1 \quad (14)$$

wherein the reference symbol D represents distance as measured from the optical axis to the outermost marginal edge of the surface-staped light source (the end surface of the first light guide), the reference symbol $\Delta$ designates deviation in the direction along the x axis between the aspherical surface expressed by the above-mentioned formula (3) and actual aspherical surface and the reference symbol $x_{max}$ denotes the maximum value of $|x|$ expressed by the formula (3).

Surface precision need not be so high in illumination optical systems. It is therefore possible to obtain an optical system having favorable light distribution characteristics so long as the optical systems satisfy the condition (6) even when actual shape of the aspherical spherical surface is deviated from the shape of aspherical surface expressed by the formula (3) as shown in FIG. 8.

Further, when the lens system satisfies the condition (5), or P is smaller than 0, it is desirable to design the lens system so as to satisfy the following conditions:

$$E \leq 0$$

$$F \leq 0$$

$$0 \leq |E \cdot D^{-3}| \leq 1.5$$

$$0 \leq |F \cdot D^{-3}| \leq 1$$

In such an optical system as shown in FIG. 7, when the focal length of the lens system 3 is represented by f, the angle formed between the optical axis and the ray emerging from each fiber of the first light guide is designated by $\theta_1$, the angle formed between this ray and the optical axis when the ray is incident on the second light guide 2 is denoted by $\theta_2$, and the distances as measured from the centers of the respective light guides are represented by $r_1$ and $r_2$ respectively, the optical system can be made to have the following relations:

$$f \tan \theta_1 = r_2 \quad (i)$$

$$r_1 = f \tan \theta_2 \quad (ii)$$

That is to say, all the rays emerging at the angle of $\theta_1$ from the first light guide 1 are condensed on the end surface of incidence of the second light guide. Similarly, all the rays emerging at the same angle are condensed on the same point. In FIG. 7, the rays $L_1$, $L_4$ and $L_7$ are condensed on a point of $r_2$, the rays $L_2$, $L_5$ and $L_8$ are condensed on a point of 0, and the rays $L_3$, $L_6$ and $L_9$ are condensed on a point of $-r_2$. All the rays emerging from the same point on the end surface of the first light guide are incident on the end surface of the second light guide at the same angle. Speaking concretely, the rays $L_1$, $L_2$ and $L_3$ are incident at the angle of $-\theta_2$, the rays $L_4$, $L_5$ and $L_6$ are incident at the angle of 0°, and the rays $L_7$, $L_8$ and $L_9$ are incident at the angle of $+\theta_2$ in FIG. 7.

Then, the following formula (iii) is obtained from the formulae (i) and (ii):

$$\tan\theta_1/\tan\theta_2 = r_2/r_1 = \beta' \quad \text{(iii)}$$

This formula gives $r_2 = \beta' r_1$ as the range of the intensity distribution on the end surface of incidence of the second light guide used in the illumination optical system shown in FIG. 7 and, when the intensity distribution on the end surface of emergence of the first light guide has a shape expressed as $I(\tan\theta) = -a\tan^2\theta + b$, the intensity distribution on the end surface of emergence of the second light guide has the same shape as that on the end surface of emergence of the first light guide, wherein $\tan\theta$ is transformed into $r_2$. This transformation means that all the rays emitted at the same angle $\theta_1$ from the first light guide are incident on the same position $r_2$ on the end surface of incidence of the second light guide.

After the transformation described above, the intensity distribution is expressed as follows:

$$I(r_2) = -r_2^2 + b$$

When $r_2$ is equal to $\beta' r_1$, the intensity distribution is expressed by the following formula (iv):

$$I(r_2) = -a\beta'^2 r_1^2 + b = 0 \quad \text{(iv)}$$

Further, when light quantity per unit area is assumed to be 1, total light quantity $$\int_0^{\beta' r_1} 2\pi r_2 \cdot I(r_2) dr_2$$

becomes $\pi r_1^2$ on the end surface of emergence of the first light guide, and the total light quantity is expressed by the following formula (V):

$$\int_0^{\beta' r_1} 2\pi \cdot r_2 \cdot I(r_2) \, dr_2 = \pi r_1^2 \quad \text{(v)}$$

From the formulae (iv) and (V), a and b are expressed as follows:

$$a = 2/\beta'^4 \times \frac{1}{r_1^2} \quad b = \frac{2}{\beta'^2}$$

Hence, $$I(r_2) = \frac{2}{\beta'^4} \cdot \frac{1}{r_1^2} \cdot r_2^2 + \frac{2}{\beta'^2}$$

Furthermore, as for the light distribution characteristic, the light intensity at a point on the first light guide located at a distance of r from the optical axis becomes the intensity of light travelling in the direction of an angle of incidence $\theta$ of light coming from the point located at the distance r and incident on the end surface of the second light guide. In other words, the light intensity distribution on the end surface of emergence of the first light guide is transformed into the light distribution characteristic of light incident on the second light guide.

In addition, this transformation means that all the rays emitted from the same point of the first light guide are incident at the same angle on the end surface of incidence of the second light guide. And the range of the light distribution characteristic is $\tan\theta_2 1/\beta' \tan\theta_1$.

Now, assuming that $\beta'$ is equal to $1/\sqrt{2}$, intensity $I(r_2)$ is expressed as follows:

$$I(r_2) = -8 \cdot \frac{1}{r_1^2} \cdot r_2^2 + 4 \quad \text{(A)}$$

Further, range of the light distribution angle is expressed by the formula given below:

$$\frac{1}{\beta'} \tan\theta = \sqrt{2} \tan\theta$$

This light distribution characteristic can be graphically represented as shown in FIG. 9A, FIG. 9B and FIG. 9C. Describing these graphs concretely, FIG. 9A illustrates intensity distribution of the light on the end surface of incidence of the second light guide expressed by the formula (A), FIG. 9B visualizes the light distribution characteristic on the end surface of incidence of the second light guide and FIG. 9C shows the light distribution characteristic taking $\theta_2$ as the abscissa. As is clear from these graphs, the illumination optical system according to the present invention can remarkably improve the light distribution characteristic on the second light guide as compared with the intensity distribution and light distribution characteristic of the secondary light source on the end surface of the first light guide.

In order to design such a lens system of the $r = \tan\theta$ type, it is sufficient to use an aspherical surface whose refractive power is strong in the vicinity of the optical axis and weakened gradually toward the marginal portion. This aspherical surface has a shape mainly similar to a hyperbolic surface of revolution.

In cases where the illumination optical system according to the present invention is to be applied to endoscopes or the similar instruments, the optical system must have a light distribution angle of at least 30° on one side at the optical axis. In order to satisfy this requirement, it is necessary to design the illumination optical system so as to satisfy any one of the combinations of the conditions mentioned above.

If f is too large to satisfy the condition (4), it will be impossible to obtain a sufficient light distribution angle and the illumination optical system will be unsuited for use with endoscopes or the similar instruments.

The conditions (5) and (6), the conditions (6) through (11) or the conditions (6), (8), (9), (12) through (14) define the shape of the aspherical surface which is similar to a hyperbolic surface. If these conditions are not satisfied, the lens system will not be of the $r = f \tan\theta$ type and light distribution will be degraded.

When the illumination optical system according to the present invention described above is to be used as an illumination device using light guides designed in two blocks, it is necessary to perform optimum illumination matched with field angles of endoscopes.

For this purpose, the present invention makes it possible to perform illumination matched with visual fields of endoscopes.

FIG. 10A and FIG. 10B illustrates illumination optical systems each of which has the characteristic of the present invention described above. In these drawings, the first light guide 1 is common, whereas the second light guides 2 and 2' as well as the illumination lenses 3 and 3' are different from each other. FIG. 10A shows a combination of a certain endoscope and the first light guide, whereas FIG. 10B illustrates a combination of another endoscope and the first light guide. Out of these illumination optical systems, the optical system shown in FIG. 10A uses a lens system having a short focal length f as the lens system 3. Accordingly, NA for incidence on the second light guide 2, namely, the angle $\theta_{1'}$ is large. On the other hand, the illumination optical system illustrated in FIG. 10B uses a lens system having a relatively long focal length f as the lens system 3, whereby NA for incidence can the second light guide 2 (angle $\theta$) is relatively small.

It is possible to vary the illumination angle $\theta'$ by using lens systems having different focal lengths as described above. Accordingly, it is possible to perform optimum illumination matched with field angles of endoscopes.

In order to obtain optimum illumination angles $\theta'$ matched with field angles of endoscopes, it is sufficient to vary power of the lens system 3 by using an adequate means, for example, by designing the lens system 3 so as to be freely attachable and detachable to and from the second light guide 2 for permitting replacement thereof, by composing the lens system 3 of a plural number of lens components so as to permit varying the airspace reserved therebetween or by using a lens having variable focal length such as a liquid crystal lens. In this case, an end surface of emergence $S_1$ of the first light guide 1 and an end surface of incidence $S_2$ of the second light guide 2 are adjusted so as to be located in the vicinity of the front focal point and the rear focal point respectively of the lens system 3.

In FIG. 11A and FIG. 11B, the end surface of emergence $S_1$ of the first light guide 1 and the end surface of incidence $S_2$ of the second light guide 2 are located at the positions conjugate with each other with regard to the lens system 3.

When radius of the end surface of emergence $S_1$ of the first light guide 1 is represented by r, illumination angle of the first light guide 1 is designated by $\theta$, focal length of the lens system 3 is denoted by f, radius of an image of the end surface of emergence of the first light guide 1 formed by the lens system 3 in the vicinity of the end surface of incidence $S_2$ of the second light guide 2 is represented by $r_1$, illumination angle of the second light guide 2 is designated by $\theta$ and the imaging magnification is denoted by $\beta_1$ in FIG. 11A, the following relations (vi) and (vii) are established:

$$\sin \theta_1 = \sin \theta / \beta_1 \quad \text{(vi)}$$

$$r_1 = r/\beta_1 \quad \text{(vii)}$$

Further, when the distance from the end surface of emergence $S_1$ of the first light guide 1 to the end surface of incidence of the second light guide 2 is represented by $l_1$, the following relation (viii) is established:

$$l_1 = f\left(2 + \beta_1 + \frac{1}{\beta_1}\right) \quad \text{(viii)}$$

Similarly, when an image of the first light guide 1 is formed in the vicinity of the end surface of incidence $S_2$ of the second light guide 2 at a magnification of $\beta_2$, different from said imaging magnification $\beta_1$, on the end surface of emergence $S_2$ of the first light guide 1 by using the lens system 3 having the same focal length as shown in FIG. 11B, we obtain the following formulae (ix), (x) and (xi):

$$\sin \theta_2 = \sin \theta / \beta_2 \quad \text{(ix)}$$

$$r_2 = r/\beta_2 \quad \text{(x)}$$

$$l_2 = f\left(2 + \beta_2 + \frac{1}{\beta_2}\right) \quad \text{(xi)}$$

wherein the reference symbol $r_2$ represents radius of image formed on the end surface of emergence of the first light guide 1 and the reference symbol $\theta_2$ designates illumination angle of the first light guide 1.

When $\beta_2$ is equal to $1/\beta_1$ in the above formulae, $l_1$ is equal to $l_2$.

As is understood from the foregoing description, it is possible to optionally set the illumination angle at two levels of $\theta_1$ and $\theta_2$ by varying location of the lens system 3 only without changing both the distance $l_1$ or $l_2$ as measured from the end surface of emergence $S_1$ of the first light guide 1 to the end surface of incidence $S_2$ of the second light guide 2, and the focal length of the lens system 3.

On an assumption of $\theta=30°$, $r=1$, $f=1$, $\beta_1 = 1\sqrt{2}$ $\beta_2=\sqrt{2}$, for example, we obtain the following values of $l_1$, $l_2$ and so on:

$$l_1 = l_2 = 4.12$$

$$\theta_1 = 45°, r_1 = 0.71$$

$$\theta_2 = 21°, r_2 = 1.41$$

When values of $l_1$, $l_2$ and f are not fixed but adjustable, it is possible to make values of $\theta_1$ and $\theta_2$ freely adjustable and set them at values optimum for visual fields of endoscopes.

DETAILED DESCRIPTION OF THE PREFERRED EMBODIMENTS

Figure 1:
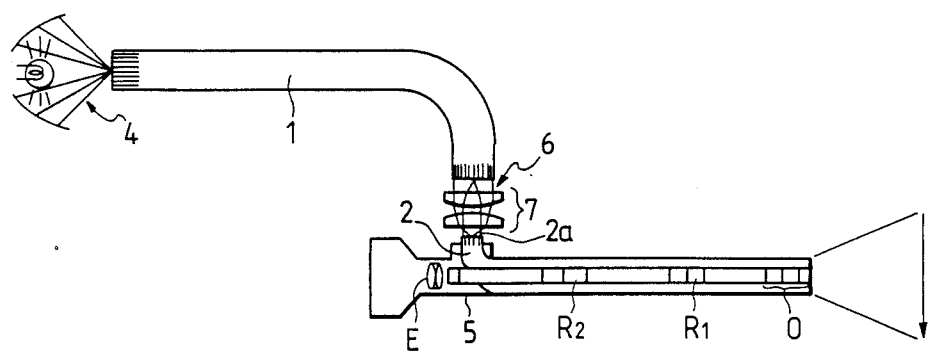
FIG. 1 shows a sectional view illustrating the composition of the conventional illumination optical system for endoscopes.
Figure 2:
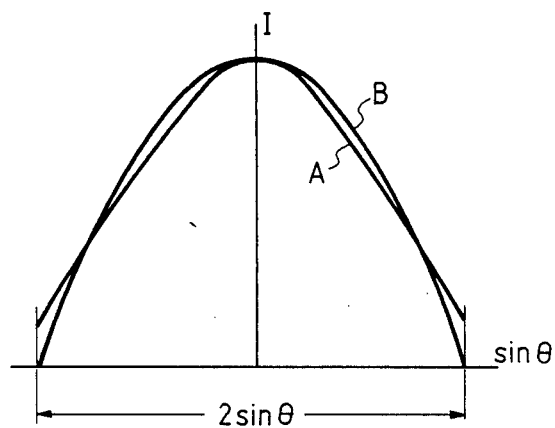
FIG. 2 shows a graph illustrating the light distribution characteristic on the end surface of emergence of the light source side light guide in said illumination optical system.
Figure 3:
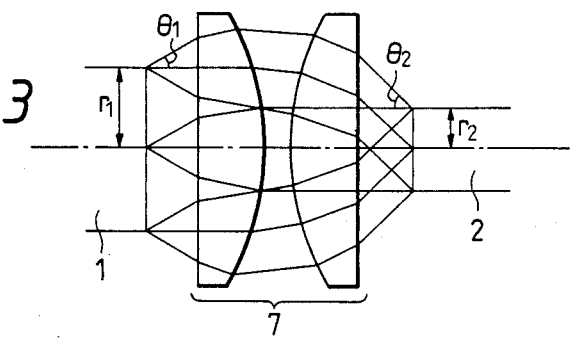
FIG. 3 shows a sectional view illustrating the conventional illumination optical system.
Figure 4:
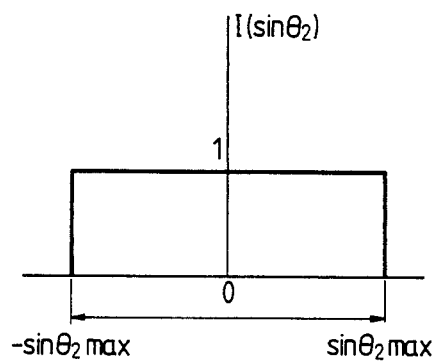
FIG. 4 and FIG. 5 show graphs illustrating the light distribution characteristics of the lens system shown in FIG. 3.
Figure 5:
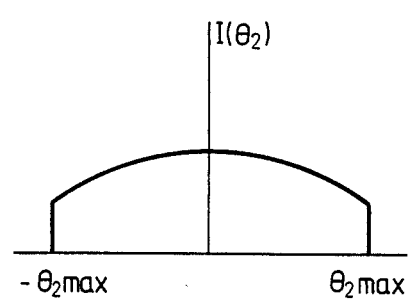
Figure 6:
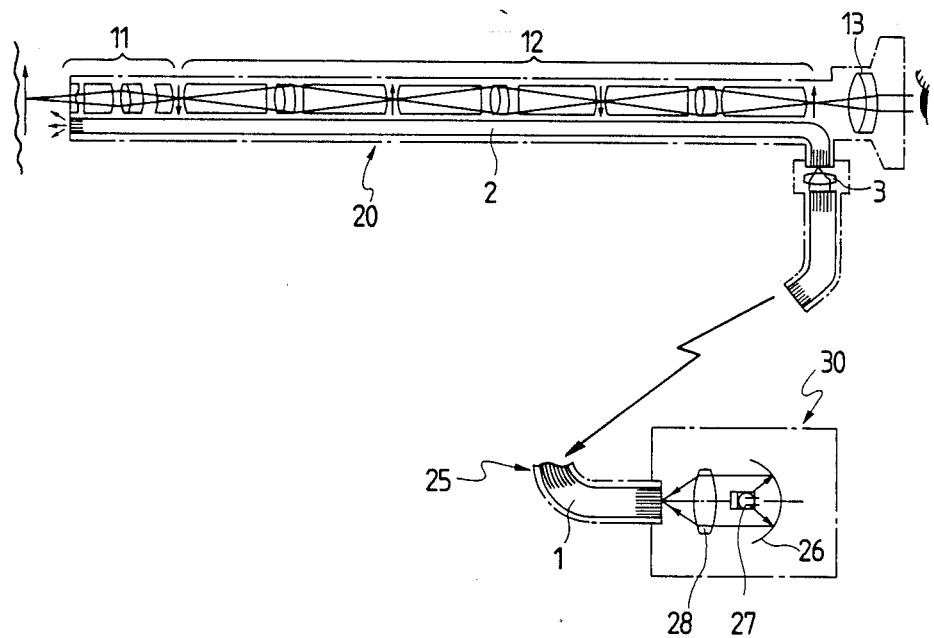
FIG. 6 shows a sectional view illustrating the composition of the endoscope equipped with light guides designed in two blocks.

Now, the present invention will be described more detailedly with the reference to the preferred Embodiments.

The Embodiments 1 through 19 of the lens system used in the illumination optical system according to the present invention are illustrated in FIG. 12 through FIG. 30 and have the following numerical data:

Embodiment 1
$f = 1.451$
$r_1 = 1.6337$ (aspherical surface)
$d = 2.1000 \quad n = 1.78472 \quad \nu = 25.70$
$r_2 = -1.6337$ (aspherical surface)
aspherical surface coefficient (1st surface)
$P = -1.0840, \quad B = 0, \quad E = 0$
$F = -0.22498 \times 10^{-2}, \quad G = 0$
(2nd surface)
$P = -1.0840, \quad B = 0, \quad E = 0$
$F = 0.22498 \times 10^{-2}, \quad G = 0$
$P_1/P_2 = 1, \quad \Delta = 0, \quad |\omega_1(D)/\omega_2(D)| = 1$
$D = 1$ Embodiment 2
$f = 1.395$
$r_1 = 1.5284$ (aspherical surface)
$d = 2.1000 \quad n = 1.78472 \quad \nu = 25.70$
$r_2 = -1.5284$ (aspherical surface)
aspherical surface coefficient (1st surface)
$P = -2.4800, \quad B = 0, \quad E = 0$
$F = 0.13488 \times 10^{-2}, \quad G = 0$
(2nd surface)
$P = -2.4800, \quad B = 0, \quad E = 0$
$F = -0.13488 \times 10^{-2}, \quad G = 0$
$P_1/P_2 = 1, \quad \Delta = 0, \quad |\omega_1(D)/\omega_2(D)| = 1$
$D = 1$ Embodiment 3
$f = 1.193$
$r_1 = 1.0455$ (aspherical surface)
$d = 2.1000 \quad n = 1.78472 \quad \nu = 25.70$
$r_2 = -1.0455$ (aspherical surface)
aspherical surface coefficient (1st surface)
$P = -4.0008, \quad B = 0, \quad E = 0$
$F = 0.19616 \times 10^{-2}, \quad G = 0$
(2nd surface)
$P = -4.0008, \quad B = 0, \quad E = 0$
$F = -0.19616 \times 10^{-2}, \quad G = 0$
$P_1/P_2 = 1, \quad \Delta = 0, \quad |\omega_1(D)/\omega_2(D)| = 1$
$D = 1$ Embodiment 4
$f = 1.102$
$r_1 = 0.9427$ (aspherical surface)
$d = 1.9510 \quad n = 1.78472 \quad \nu = 25.70$
$r_2 = -0.9427$ (aspherical surface)
aspherical surface coefficient (1st surface)
$P = -5.5981, \quad B = 0, \quad E = 0.12574 \times 10^{-2}$
$F = 0.21918 \times 10^{-2}, \quad G = -0.10968 \times 10^{-6}$
(2nd surface)
$P = -5.5981, \quad B = 0$
$E = -0.12574 \times 10^{-2}$
$F = -0.21918 \times 10^{-2}$
$G = 0.10968 \times 10^{-6}$
$P_1/P_2 = 1, \quad \Delta = 0, \quad |\omega_1(D)/\omega_2(D)| = 1$
$D = 1$ Embodiment 5
$f = 1.170$
$r_1 = 1.5204$ (aspherical surface)
$d = 1.7143 \quad n = 1.88300 \quad \nu = 40.78$
$r_2 = -1.5204$ (aspherical surface)
aspherical surface coefficient (1st surface)
$P = -2.8145, \quad B = 0, \quad E = 0$
$F = 0.60462 \times 10^{-3}, \quad G = 0$
(2nd surface)
$P = -2.8145, \quad B = 0, \quad E = 0$
$F = -0.60462 \times 10^{-3}, \quad G = 0$
$P_1/P_2 = 1, \quad \Delta = 0, \quad |\omega_1(D)/\omega_2(D)| = 1$
$D = 1$ Embodiment 6
$f = 0.974$
$r_1 = 1.0788$ (aspherical surface)
$d = 1.7143 \quad n = 1.88300 \quad \nu = 40.78$
$r_2 = -1.0788$ (aspherical surface)
aspherical surface coefficient (1st surface)
$P = -5.6395, \quad B = 0, \quad E = 0$
$F = 0.23377 \times 10^{-2}, \quad G = 0$
(2nd surface)
$P = -5.6395, \quad B = 0, \quad E = 0$
$F = -0.23377 \times 10^{-2}, \quad G = 0$
$P_1/P_2 = 1, \quad \Delta = 0, \quad |\omega_1(D)/\omega_2(D)| = 1$
$D = 1$ Embodiment 7
$f = 1.141$
$r_1 = 1.2767$ (aspherical surface)
$d = 2.3000 \quad n = 1.78472 \quad \nu = 25.70$
$r_2 = -0.6241$ (aspherical surface)
aspherical surface coefficient (1st surface)
$P = -2.5679, \quad B = 0, \quad E = 0.14389 \times 10^{-1}$
$F = 0.21916 \times 10^{-2}$
$G = -0.10968 \times 10^{-6}$
(2nd surface)
$P = -10.1148, \quad B = 0$
$E = 0.14898 \times 10^{-1}$
$F = -0.21926 \times 10^{-2}$
$G = 0.10967 \times 10^{-6}$
$P_1/P_2 = 0.2541, \quad \Delta = 0, \quad |\omega_1(D)/\omega_2(D)| = 2.154$
$D = 1$ Embodiment 8
$f = 1.111$
$r_1 = 1.1013$ (aspherical surface)
$d = 1.9998 \quad n = 1.78472 \quad \nu = 25.70$
$r_2 = -0.8432$ (aspherical surface)
aspherical surface coefficient (1st surface)
$P = -0.6443, \quad B = 0,$
$E = -0.33017 \times 10^{-1}, \quad F = 0.21916 \times 10^{-2}$
$G = -0.10968 \times 10^{-6}$
(2nd surface)
$P = -17.7885, \quad B = 0$
$E = -0.31311 \times 10^{-1}$
$F = -0.21931 \times 10^{-2}$
$G = 0.10967 \times 10^{-6}$
$P_1/P_2 = 0.036, \quad \Delta = 0, \quad |\omega_1(D)/\omega_2(D)| = 1.649$
$D = 1$ -continued Embodiment 9
f = 1.136
$r_1$ = 1.1601 (aspherical surface)
d = 2.1764    n = 1.78472    $\nu$ = 25.70
$r_2$ = −0.6745 (aspherical surface)
　　　aspherical surface coefficient
(1st surface)
P = −1.8617,  B = 0,  E = 0.14226 × $10^{-1}$
F = 0.21915 × $10^{-2}$
G = −0.10968 × $10^{-6}$
(2nd surface)
P = −13.9993,  B = 0
E = 0.12040 × $10^{-1}$
F = −0.21925 × $10^{-2}$
G = 0.10967 × $10^{-6}$
$P_1/P_2$ = 0.133,  Δ = 0,  $|\omega_1(D)/\omega_2(D)|$ = 3.15
D = 1
Embodiment 10
f = 1.069
$r_1$ = 1.2636 (aspherical surface)
d = 1.8337    n = 1.78472    $\nu$ = 25.70
$r_2$ = −0.9030 (aspherical surface)
　　　aspherical surface coefficient
(1st surface)
P = −0.9365,  B = 0,  E = 0.80216 × $10^{-2}$
F = 0.21913 × $10^{-2}$
G = −0.10968 × $10^{-6}$
(2nd surface)
P = −14.9547,  B = 0
E = 0.18359 × $10^{-1}$
F = −0.21923 × $10^{-2}$
G = 0.10967 × $10^{-6}$
$P_1/P_2$ = 0.063,  Δ = 0,  $|\omega_1(D)/\omega_2(D)|$ = 3.778
D = 1
Embodiment 11
f = 1.057
$R_1$ = 1.2119 (aspherical surface)
d = 1.6097    n = 1.78472    $\nu$ = 25.70
$r_2$ = −1.0931 (aspherical surface)
　　　aspherical surface coefficient
(1st surface)
P = −1.5870,  B = 0,  E = 0.23812 × $10^{-1}$
F = 0.21914 × $10^{-2}$
G = −0.10968 × $10^{-6}$
(2nd surface)
P = −15.7719,  B = 0
E = −0.41582 × $10^{-2}$
F = −0.21923 × $10^{-2}$
G = 0.10967 × $10^{-6}$
$P_1/P_2$ = 0.101,  Δ = 0,  $|\omega_1(D)/\omega_2(D)|$ = 2.481
D = 1
Embodiment 12
f = 1.170
$r_1$ = 2.5702 (aspherical surface)
$d_1$ = 1.1600    $n_1$ = 1.88300    $\nu_1$ = 40.78
$r_2$ = −3.2305 (aspherical surface)
$d_2$ = 0.0857
$r_3$ = 3.2305 (aspherical surface)
$d_3$ = 1.1600    $n_2$ = 1.88300    $\nu_2$ = 40.78
$r_4$ = −2.5702 (aspherical surface)
　　　aspherical surface coefficient
(1st surface)
P = 2.5126,  B = 0,  E = −0.76810 × $10^{-1}$
F = 0.90435 × $10^{-7}$,  G = 0
(2nd surface)
P = −8.7600,  B = 0
E = −0.22112 × $10^{-1}$
F = −0.67696 × $10^{-6}$,  G = 0
(3rd surface)
P = −8.7600,  B = 0,  E = 0.22112 × $10^{-1}$
F = 0.67696 × $10^{-6}$,  G = 0
(4th surface)
P = 2.5126,  B = 0
E = 0.76810 × $10^{-1}$
F = −0.90435 × $10^{-7}$,  G = 0
Embodiment 13
f = 1.075

-continued $r_1$ = 1.1739 (aspherical surface)
$d_1$ = 1.6234    $n_1$ = 1.78472    $\nu_1$ = 25.76
$r_2$ = −1.1739 (aspherical surface)
　　　aspherical surface coefficient
(1st surface)
P = −2.5000,  B = 0
E = −0.76732 × $10^{-1}$
F = 0.35388 × $10^{-1}$,  G = −0.45172 × $10^{-7}$
(2nd surface)
P = −2.5000,  B = 0
E = 0.76732 × $10^{-1}$
F = −0.35388 × $10^{-1}$,  G = 0.45172 × $10^{-7}$
$P_1/P_2$ = 1,  Δ = 0,  $|\omega_1(D)/\omega_2(D)|$ = 1
D = 1
Embodiment 14
f = 1.077
$r_1$ = 1.2822 (aspherical surface)
$d_1$ = 1.4067    $n_1$ = 1.78472    $\nu_1$ = 25.76
$r_2$ = −1.2822 (aspherical surface)
　　　aspherical surface coefficient
(1st surface)
P = −0.5000,  B = 0,  E = −0.14713
F = 0.52671 × $10^{-1}$,  G = 0.87334 × $10^{-8}$
(2nd surface)
P = −0.5000,  B = 0,  E = 0.14713
F = −0.52671 × $10^{-1}$,  G = −0.87334 × $10^{-8}$
$P_1/P_2$ = 1,  Δ = 0,  $|\omega_1(D)/\omega_2(D)|$ = 1
D = 1
Embodiment 15
f = 1.077
$r_1$ = 1.2855 (aspherical surface)
$d_1$ = 1.3991    $n_1$ = 1.78472    $\nu_1$ = 25.76
$r_2$ = −1.2855 (aspherical surface)
　　　aspherical surface coefficient
(1st surface)
P = 0,  B = 0,  E = −0.17484
F = 0.55298 × $10^{-1}$,  G = 0.17356 × $10^{-7}$
(2nd surface)
P = 0,  B = 0,  E = 0.17484
F = −0.55298 × $10^{-1}$,  G = −0.17356 × $10^{-7}$
$P_1/P_2$ = 1,  Δ = 0,  $|\omega_1(D)/\omega_2(D)|$ = 1
D = 1
Embodiment 16
f = 1.077
$r_1$ = 1.2942 (aspherical surface)
$d_1$ = 1.3786    $n_1$ = 1.78472    $\nu_1$ = 25.76
$r_2$ = −1.2942 (aspherical surface)
　　　aspherical surface coefficient
(1st surface)
P = 0.5000,  B = 0,  E = −0.19891
F = 0.47206 × $10^{-1}$,  G = −0.48882 × $10^{-8}$
(2nd surface)
P = 0.5000,  B = 0,  E = 0.19891
F = −0.47206 × $10^{-1}$,  G = -.48882 × $10^{-8}$
$P_1/P_2$ = 1,  Δ = 0,  $|\omega_1(D)/\omega_2(D)|$ = 1
D = 1
Embodiment 17
f = 1.078
$r_1$ = 1.3999 (aspherical surface)
$d_1$ = 1.0990    $n_1$ = 1.78472    $\nu_1$ = 25.76
$r_2$ = −1.3999 (aspherical surface)
　　　aspherical surface coefficient
(1st surface)
P = 1.0000, B = 0,  E = −0.17071
F = 0.11270 × $10^{-1}$,  G = −0.85546 × $10^{-7}$
(2nd surface)
P = 1.0000,  B = 0,  E = 0.17071
F = −0.11270 × $10^{-1}$,  G = 0.85546 × $10^{-7}$
$P_1/P_2$ = 1,  Δ = 0,  $|\omega_1(D)/\omega_2(D)|$ = 1
D = 1
Embodiment 18
F = 1.079
$r_1$ = 1.5171 (aspherical surface)
$d_1$ = 0.7215    $n_1$ = 1.78472    $\nu_1$ = 25.76
$r_2$ = −1.5171 (aspherical surface)
　　　aspherical surface coefficient
(1st surface)

-continued

P = 1.2000, B = 0, E = −0.13557
F = −0.24303 × 10⁻², G = −0.10944 × 10⁻⁶
(2nd surface)
P = 1.2000, B = 0, E = 0.13557
F = 0.24303 × 10⁻², G = 0.10944 × 10⁻⁶
P₁/P₂ = 1, Δ = 0, |ω₁(D)/ω₂(D)| = 1
D = 1

Embodiment 19
f = 0.987
r₁ = 4.9437 (aspherical surface)
d₁ = 1.0408   n₁ = 1.78472   ν₁ = 25.76
r₂ = ∞
d₂ = 0.3934
r₃ = 0.7758 (aspherical surface)
d₃ = 1.0417   n₂ = 1.78472   ν₂ = 25.76
r₄ = ∞ aspherical surface coefficient
(1st surface)
P = 1.0053, B = 0, E = 0.37292 × 10⁻¹
F = 0.55715 × 10⁻⁴, G = 0
(3rd surface)
P = −2.3790, B = 0, E = 0.31172 × 10⁻¹
F = 0.94539 × 10⁻⁸, G = 0
Δ = 0, D = 1

The following numerical tables show the value of the formulas $(d\theta/dr_1)/(d\theta/dr_1)r_1=0$ and $f/\sqrt{F^2-r_1^2}$ recited in the above-mentioned embodiments, wherein $(d\theta/dr_1)/(d\theta/dr_1)r_1-0$ is represented by a symbol I and $f/\sqrt{f^2-r_1^2}$ is represented by a symbol II.

Embodiment 1
| $r_1$ | 0.2 | 0.4 | 0.6 | 0.8 | 1.0 | 1.076 |
| I | 0.691 | 0.703 | 0.739 | 0.837 | 1.244 | 11.914 |
| II | 1.010 | 1.040 | 1.098 | 1.199 | 1.380 | 1.491 |

Embodiment 2
| $r_1$ | 0.2 | 0.4 | 0.6 | 0.8 | 1.0 | 1.133 |
| I | 0.711 | 0.704 | 0.710 | 0.746 | 0.912 | 5.866 |
| II | 1.010 | 1.044 | 1.108 | 1.221 | 1.434 | 1.659 |

Embodiment 3
| $r_1$ | 0.2 | 0.4 | 0.6 | 0.8 | 1.0 | 1.09 |
| I | 0.836 | 0.846 | 0.811 | 0.724 | 0.815 | 6.903 |
| II | 1.014 | 1.061 | 1.157 | 1.348 | 1.834 | 2.460 |

Embodiment 4
| $r_1$ | 0.2 | 0.4 | 0.6 | 0.8 | 1.0 | 1.1 | 1.102 |
| I | 0.996 | 0.954 | 0.731 | 0.501 | 0.435 | 0.445 | 0.447 |
| II | 1.17 | 1.073 | 1.192 | 1.454 | 2.38 | 16.606 | |

Embodiment 5
| $r_1$ | 0.2 | 0.4 | 0.6 | 0.8 | 0.967 |
| I | 0.845 | 0.833 | 0.850 | 0.985 | 8.953 |
| II | 1.015 | 1.064 | 1.165 | 1.370 | 1.776 |

Embodiment 6
| $r_1$ | 0.2 | 0.4 | 0.6 | 0.8 | 0.974 |
| I | 0.993 | 0.912 | 0.732 | 0.560 | 0.547 |
| II | 1.022 | 1.097 | 1.269 | 1.753 | |

Embodiment 7
| $r_1$ | 0.2 | 0.4 | 0.6 | 0.8 | 1 | 1.140 |
| I | 0.911 | 0.878 | 0.657 | 0.462 | 0.375 | 0.366 |
| II | 1.016 | 1.068 | 1.176 | 1.402 | 2.077 | 23.89 |

Embodiment 8
| $r_1$ | 0.2 | 0.4 | 0.6 | 0.8 | 1.0 | 1.110 |
| I | 0.908 | 0.865 | 0.665 | 0.453 | 0.405 | 0.514 |
| II | 1.017 | 1.072 | 1.188 | 1.441 | 2.295 | 23.574 |

Embodiment 9
| $r_1$ | 0.2 | 0.4 | 0.6 | 0.8 | 1.0 | 1.135 |
| I | 0.910 | 0.877 | 0.657 | 0.462 | 0.374 | 0.360 |
| II | 1.016 | 1.068 | 1.178 | 1.408 | 2.108 | 23.838 |

Embodiment 10
| $r_1$ | 0.2 | 0.4 | 0.6 | 0.8 | 1.0 | 1.068 |
| I | 0.912 | 0.818 | 0.662 | 0.508 | 0.379 | 0.339 |
| II | 1.018 | 1.078 | 1.208 | 1.508 | 2.829 | 23.103 |

Embodiment 11
| $r_1$ | 0.2 | 0.4 | 0.6 | 0.8 | 1.0 | 1.056 |
| I | 0.914 | 0.802 | 0.652 | 0.567 | 0.596 | 0.639 |
| II | 1.018 | 1.080 | 1.215 | 1.530 | 3.087 | 22.995 |

Embodiment 12
| $r_1$ | 0.2 | 0.4 | 0.6 | 0.8 | 1.0 | 1.169 |
| I | 0.847 | 0.825 | 0.796 | 0.775 | 0.808 | 1.754 |
| II | 1.015 | 1.064 | 1.165 | 1.37 | 1.926 | 24.192 |

Embodiment 13
| $r_1$ | 0.2 | 0.4 | 0.6 | 0.8 | 1 |
| I | 0.974 | 0.906 | 0.735 | 0.452 | 0.564 |
| II | 1.018 | 1.077 | 1.205 | 1.497 | 2.725 |

Embodiment 14
| $r_1$ | 0.2 | 0.4 | 0.6 | 0.8 | 1 |
| I | 0.977 | 0.906 | 0.739 | 0.446 | 0.606 |
| II | 1.018 | 1.077 | 1.204 | 1.494 | 2.693 |

Embodiment 15
| $r_1$ | 0.2 | 0.4 | 0.6 | 0.8 | 1 |
| I | 0.977 | 0.907 | 0.738 | 0.446 | 0.608 |
| II | 1.018 | 1.077 | 1.204 | 1.494 | 2.693 |

Embodiment 16
| $r_1$ | 0.2 | 0.4 | 0.6 | 0.8 | 1 |
| I | 0.977 | 0.907 | 0.739 | 0.445 | 0.616 |
| II | 1.018 | 1.077 | 1.204 | 1.494 | 2.693 |

Embodiment 17
| $r_1$ | 0.2 | 0.4 | 0.6 | 0.8 | 1 |
| I | 0.978 | 0.908 | 0.741 | 0.438 | 0.701 |
| II | 1.018 | 1.077 | 1.204 | 1.492 | 2.678 |

Embodiment 18
| $r_1$ | 0.2 | 0.4 | 0.6 | 0.8 | 1 |
| I | 0.98 | 0.91 | 0.741 | 0.437 | 0.745 |
| II | 1.018 | 1.077 | 1.203 | 1.49 | 2.662 |

Embodiment 19
| $r_1$ | 0.2 | 0.4 | 0.6 | 0.8 | 0.987 |
| I | 0.853 | 0.628 | 0.516 | 0.505 | 0.546 |
| II | 1.021 | 1.094 | 1.259 | 1.707 | 22.22 |

Out of these Embodiments, each of the Embodiments 1 through 6 and the Embodiments 13 through 18 consists of a single lens component having aspherical surfaces on both the sides thereof. Accordingly, the lens component can be manufactured by press molding with a single type of mold and at a low cost.

Each of the Embodiments 7 through 11 consists of a single lens component having aspherical surfaces of different shapes and has higher performance.

Each of the Embodiments 12 and 19 consists of two lens components having aspherical surfaces and exhibits performance higher than that of the lens system consisting of a single aspherical lens component.

The lens systems illustrated as the Embodiments must have certain short focal lengths f as defined by the condition (4) for improving light distribution. For this purpose, the lens components must have high curvature on the surfaces thereof. If curvature is enhanced on the convex surface located on the side of the second light guide 2, however, the light emerging from the first light guide 1 will be totally reflected by the marginal portion of said convex surface, thereby causing loss of light quantity or degrading light distribution. In order to obtain light distribution uniform even at the marginal portion by preventing such loss of light quantity, it is necessary to design the lens system so as to satisfy the following conditions (16) and (17):

$$P_1 P_2 \leq 2 \qquad (16)$$

$$|\omega_1(D)/\omega_2(D)| \geq 0.5 \qquad (17)$$

wherein the reference symbols $P_1$ and $P_2$ represent the conical coefficients of expressing shapes of the first and second aspherical surfaces, the reference symbol $\omega_1(D)$ designates inclination angle of the surface located on the side of the first light guide 1 relative to the y axis (the axis perpendicular to the optical axis) at a point located at a distance of D from the optical axis, and the reference symbol $\omega_2(D)$ denotes inclination angle of the surface located on the side of the second light guide 2 relative to the y axis at a point of located at a distance of D from the optical axis. In addition, the reference symbol D represents radius of the first light guide.

The condition (16) means that $P_2$ is larger than $P_1$ when these coefficients are compared with each other. The light incident in parallel to the optical axis is apt to have a large angle of incidence on the second surface since said light is refracted by the first surface. Accordingly, when the curvature of the second surface is not lower than that of the first surface, the light incident from the marginal portion of the lens component is totally reflected by the second surface, thereby reducing the rays attaining to the marginal portion of the visual field. The condition (16) has been adopted for preventing the loss of light quantity described above.

The condition (17) means that the inclination angle of the surface located on the side of the first light guide 1 relative to the y axis at the point located at a radial distance of D is comparatively larger than the inclination angle of the surface located on the side of the second light guide 2 relative to the y axis at the point located at the radial distance D.

If the condition (16) or (17) is not satisfied, the convex surface including the aspherical surface and located on the side of the second light guide will have relatively large inclination at the marginal portion thereof and light quantity will be reduced due to total reflection.

Figure 7:
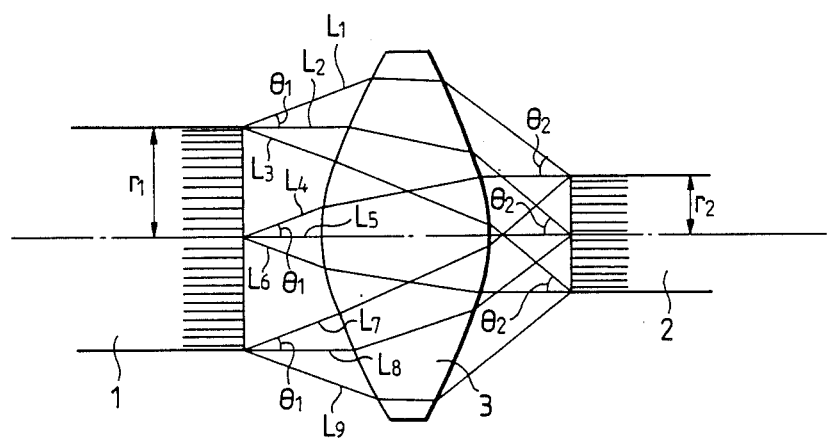
FIG. 7 shows a sectional view illustrating the illumination optical system according to the present invention.
Figure 8:
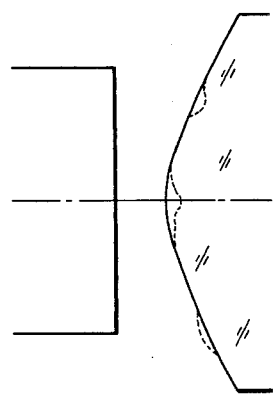
FIG. 8 shows a diagram illustrating shape of an aspherical surface.
Figure 9A:
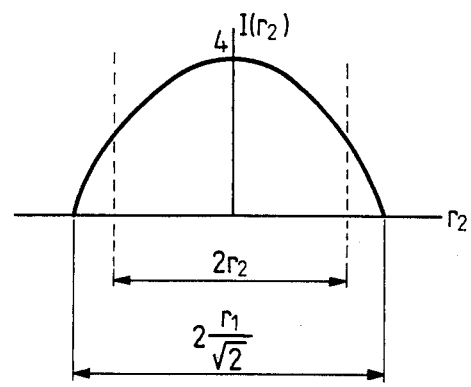
FIG. 9A, FIG. 9B and FIG. 9C show graphs illustrating light distribution characteristics of the illumination optical system according to the present invention.
Figure 9B:
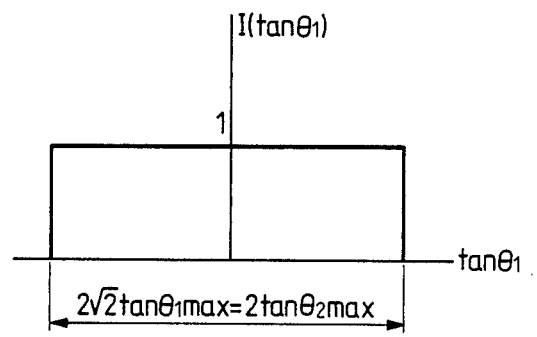
Figure 9C:
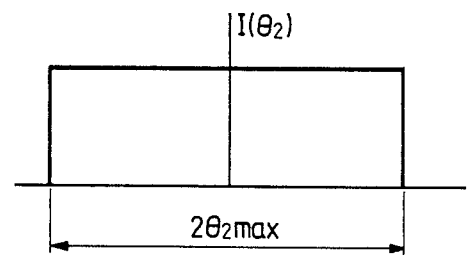
Figure 10A:
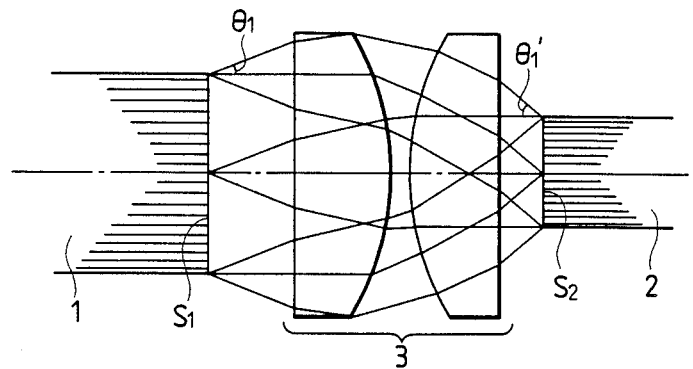
FIG. 10A, FIG. 10B, FIG. 11A and FIG. 11B show sectional views illustrating composition of the optical system wherein the illumination optical system according to the present invention is used in light guides designed as two blocks.
Figure 10B:
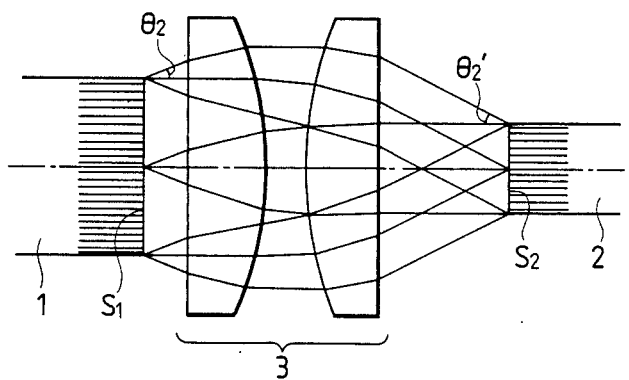
Figure 11A:
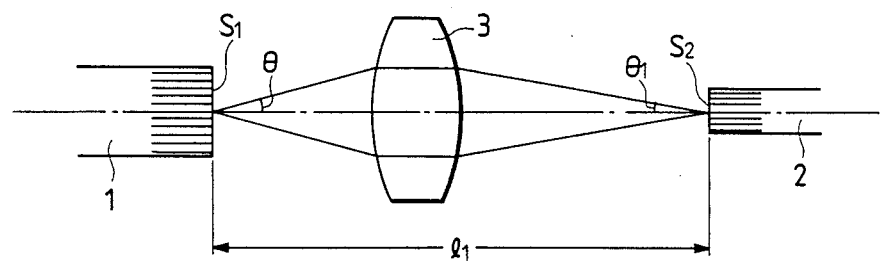
Figure 11B:
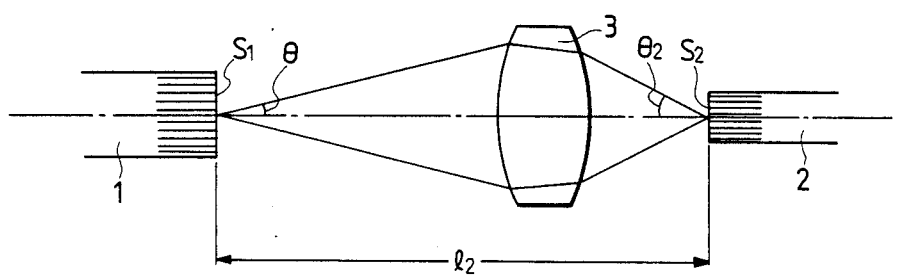
Figure 12:
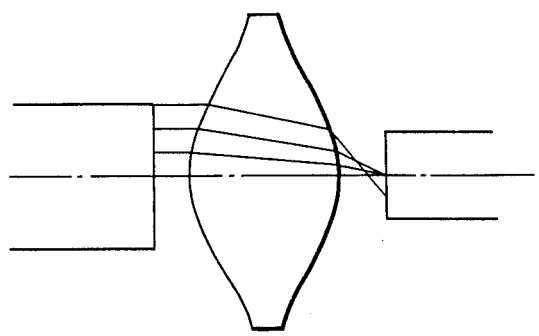
FIG. 12 through FIG. 30 stow sectional views illustrating compositions of Embodiments 1 through 19 of the lens system used in the illumination optical system according to the present invention.
Figure 13:
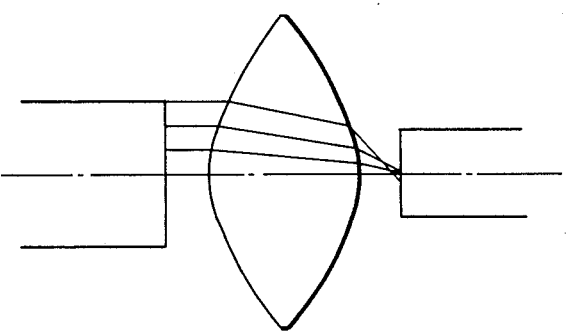
Figure 14:
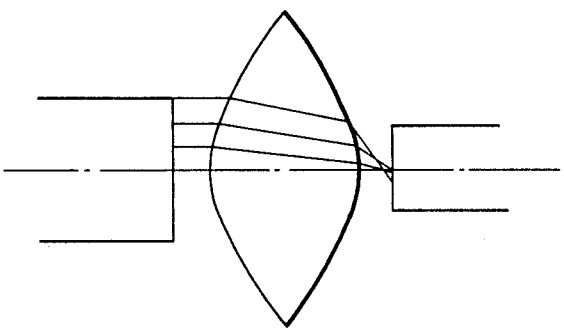
Figure 15:
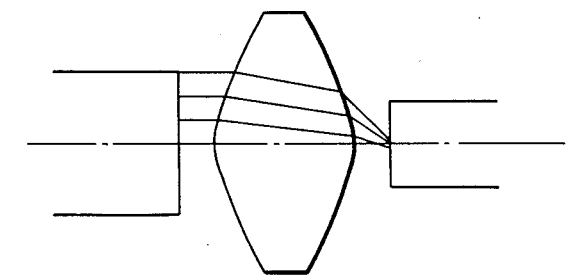
Figure 16:
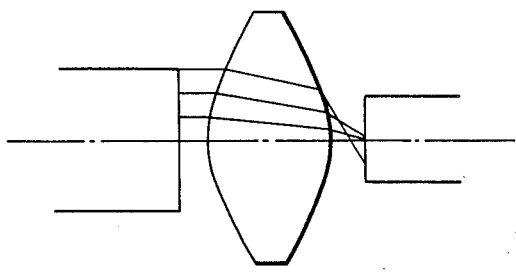
Figure 17:
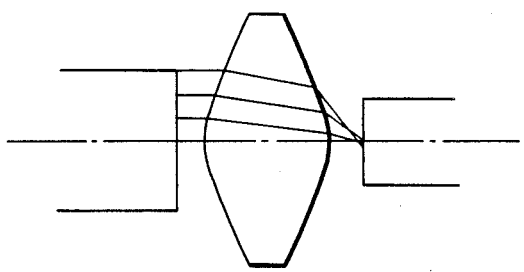
Figure 18:
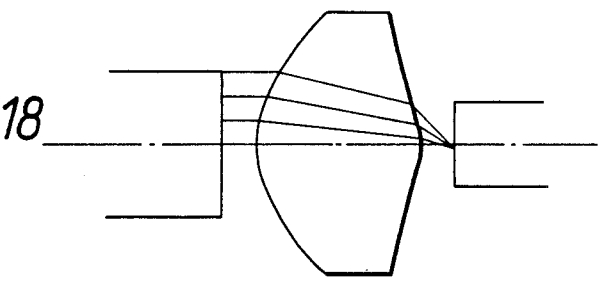
Figure 19:
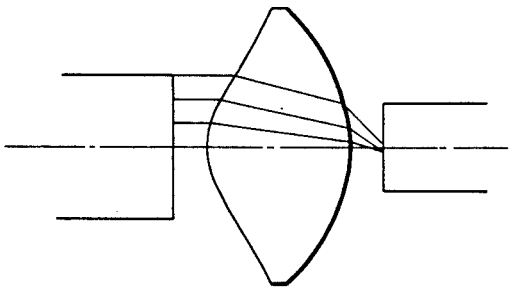
Figure 20:
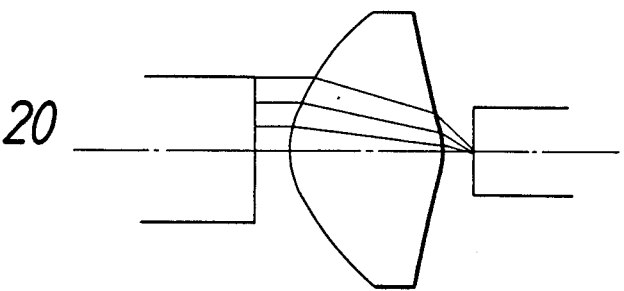
Figure 21:
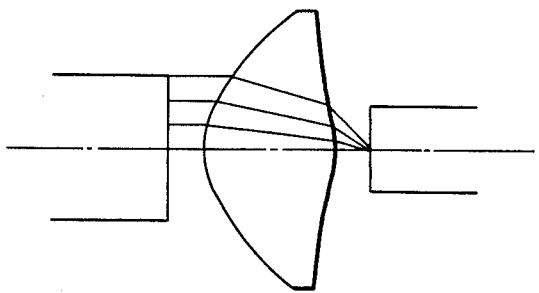
Figure 22:
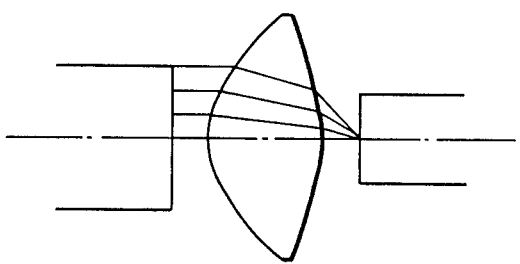
Figure 23:
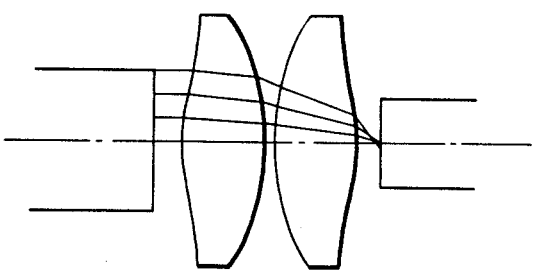
Figure 24:
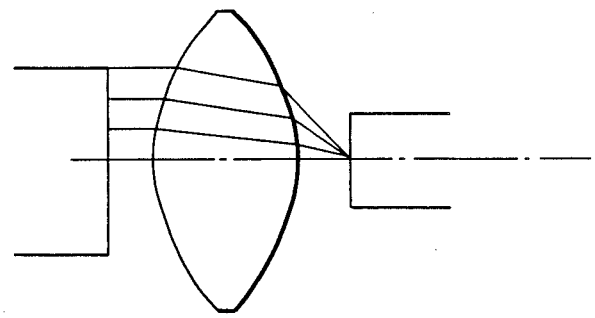
Figure 25:
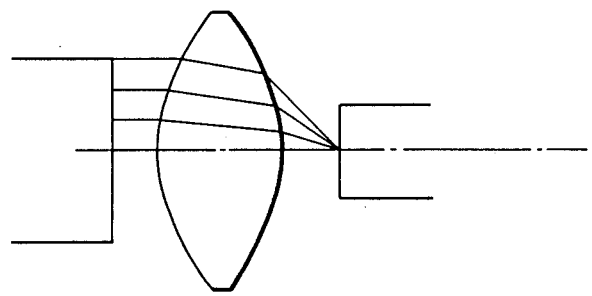
Figure 26:
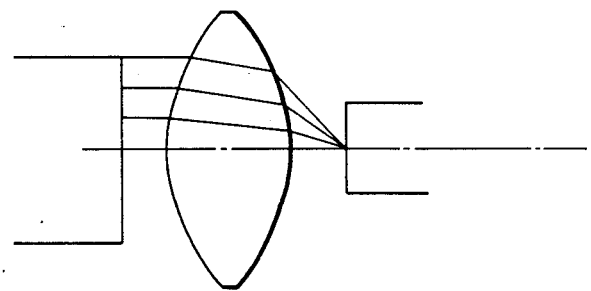
Figure 27:
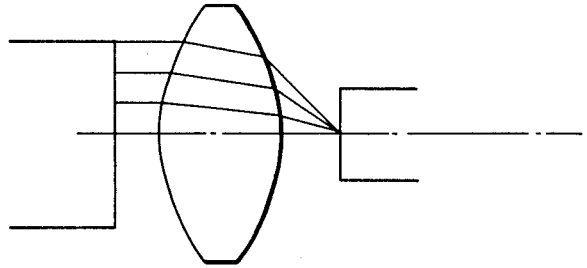
Figure 28:
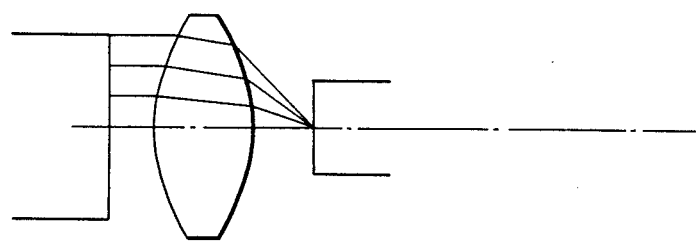
Figure 29:
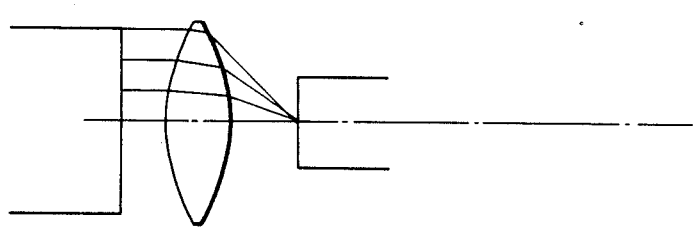
Figure 30:
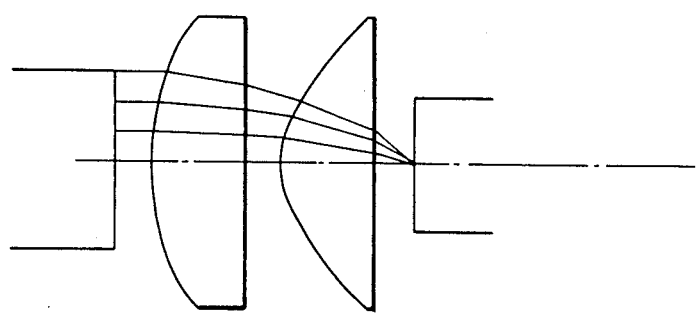

The conditions (1) through (17) described above define ranges of the paraxial rays having angles of emergence relatively parallel to the optical axis (the rays $L_2$, $L_5$ and $L_8$ shown in FIG. 7) out of the rays emerging from the first light guide.

By the way, the rays emerging from the first light guide 1 have sufficient quantities generally within a range up to 30° relative to the optical axis. It is desirable that these offaxial rays (the rays $L_1$, $L_3$, $L_4$, $L_6$, $L_7$, and $L_9$ shown in FIG. 7) are condensed like the axial rays.

However, a lens surface having the shape like a hyperbolic surface satisfying the conditions (1) through (17) has curvature abruptly lowered from the optical axis toward the marginal portion, thereby lowering convergence of the offaxial rays and reducing quantity of the rays incident on the second light guide 2. In order to prevent this reduction of light quantity, it is desirable to design a lens surface in the lens system facing the first light guide and having different portions for passing the paraxial ray and the offaxial ray an aspherical surface including portions whose curvature is gradually lowered as they are farther from the optical axis. In addition, it is preferable to design the portions outside said portions (the portions farther from the optical axis than said portions are) of said aspherical surface so as to have gradually enhanced curvature or, when two or more convex surfaces are arranged in the lens system (i.e., when the lens system consists of two or more lens components), to design a surface other than said aspherical surface as an aspherical surface including portions whose curvature is gradually enhanced as the portions are farther from the optical axis.

Further, the illumination optical system illustrated as the Embodiment 19 has a small outside diameter and favorable light distribution characteristic. Since a light guide generally has a large NA as already described above, the aspherical lens components described as the Embodiments 1 through 11 and the Embodiments 13 through 18 have large outside diameters and may be inconvenient for use in illumination optical systems for endoscopes and the similar instruments. In order to obtain a lens system having a smaller outside diameter, it is desirable to adopt a composition like that of the Embodiment 19. In the illumination optical system described as the Embodiment 19, an aspherical surface having curvature gradually lowered toward the marginal portion is arranged as the first surface of the lens system and a lens surface having the shape like a hyperbolic aspherical surface satisfying the condition (1) is used as the third surface so that the rays emerging at large NA's from the portions close to the outer circumference of the end surface of emergence of the first light guide 1 are not so apart from the optical axis. Furthermore, loss of light quantity due to total reflection is minimized in the Embodiment 19 wherein the rays are refracted by the surfaces more gradually than in the other Embodiments each consisting of a single lens component.

Figure 31:
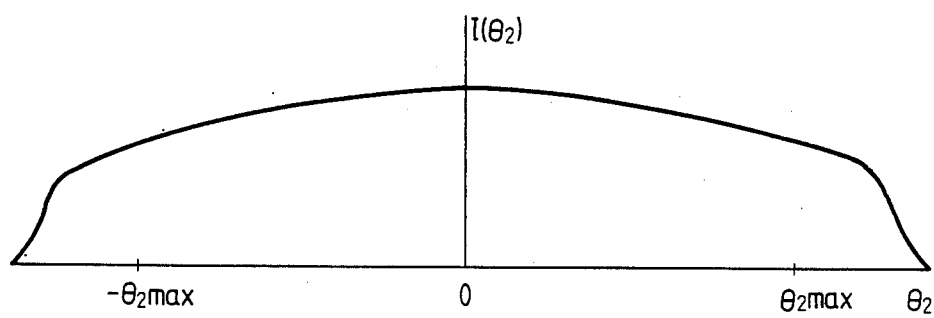
FIG. 31 show a graph illustrating the light distribution characteristic of the conventional lens system.
Figure 32:
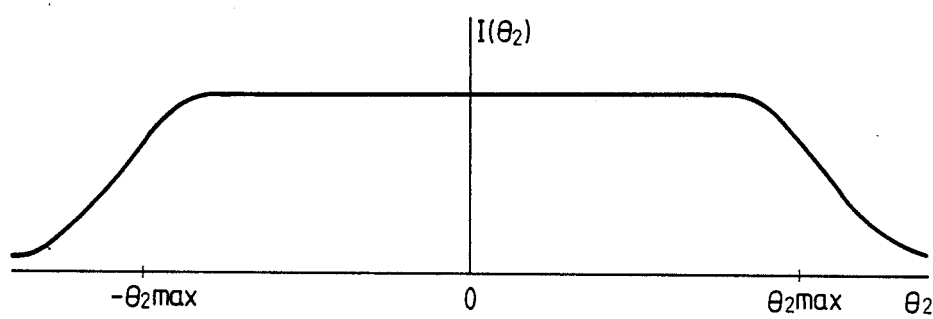
FIG. 32 and FIG. 33 show graphs illustrating light distribution characteristics of the Embodiments 4 and 11 of the lens system according to the present invention.
Figure 33:
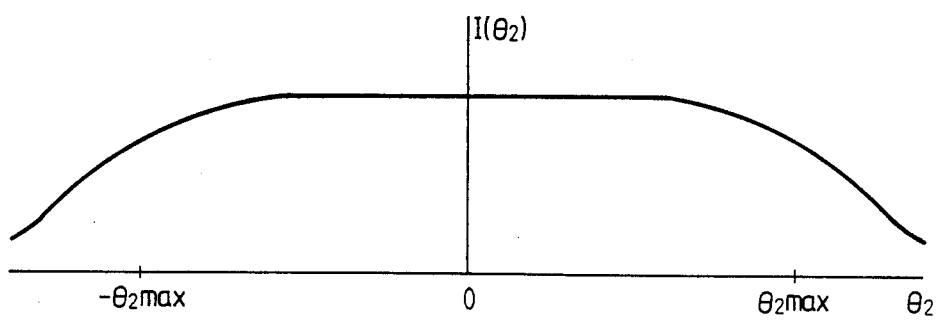

FIG. 31 illustrates the light distribution characteristic of the lens system as viewed on the end surface of incidence of the second light guide in the conventional illumination optical system. In contrast, FIG. 32 and FIG. 33 illustrate light distribution characteristics of the Embodiments 4 and 11 respectively of the illumination optical system according to the present invention.

As is clear from these drawings, the Embodiments of the present invention has the light distribution characteristics more favorable than that of the conventional illumination optical system.

The lens system used in the illumination optical system according to the present invention may be modified as described below within the range satisfying the conditions described above.

Figure 34:
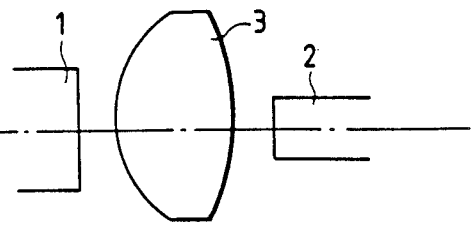
FIG. 34 through FIG. 55 show sectional views illustrating modified examples of the illumination optical system according to the present invention.

The lens system shown in FIG. 34 has an optical axis which is shifted in parallel to the optical axis of the illumination optical system.

Figure 35:
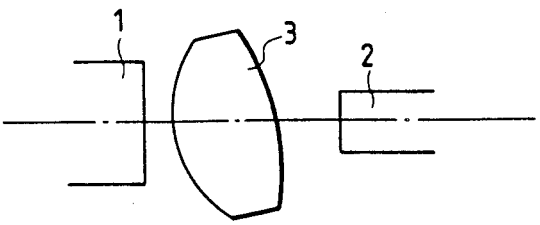

The lens system illustrated in FIG. 35 has an optical axis which is inclined relative to the optical axis of the illumination optical system.

Figure 36:
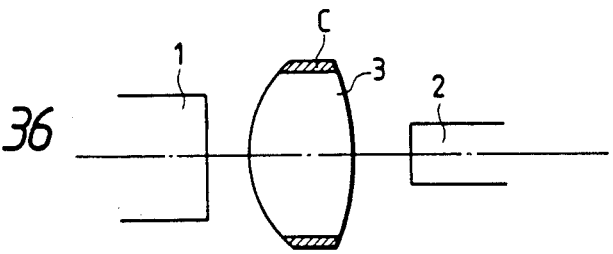
Figure 37:
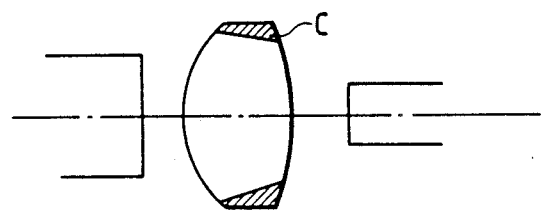

In each of the lens systems illustrated in FIG. 36 and FIG. 37, a clad layer C of a material having a refractive index lower than that of the lens component is formed on the outer circumference of the lens component. The boundary between the lens component and the clad layer is inclined in the modification example shown in FIG. 36.

Figure 38:
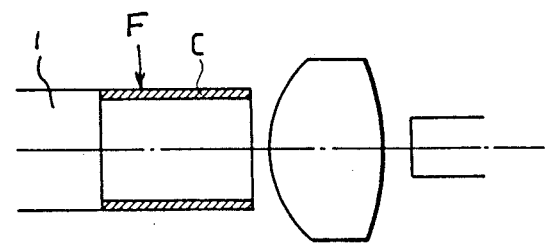
Figure 39:
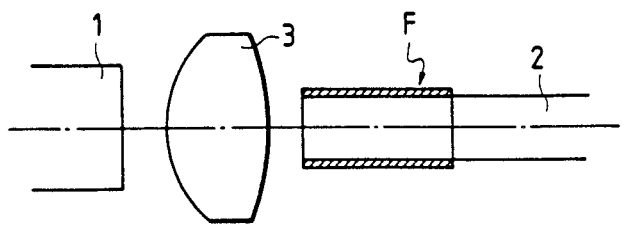
Figure 40:
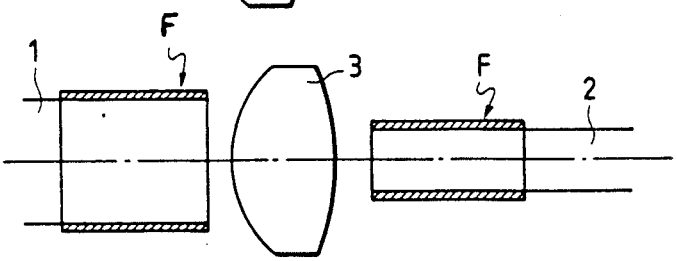

A single fiber F (an optical element composed of a bar of glass or plastic covered on the outer circumference thereof with a layer having a refractive index lower than that of the bar for totally reflecting light by the boundary layer) is arranged between the lens component and the first light guide 1 in the lens system shown in FIG. 38, between the lens component and the second light guide 2 in the lens system illustrated in FIG. 39, and on each side of the lens component in the lens system illustrated in FIG. 40.

Figure 41:
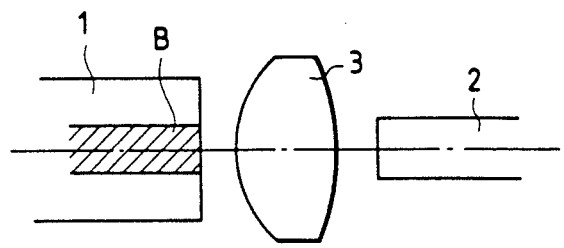

In the illumination optical system illustrated in FIG. 41, an opaque bar-shaped member B is arranged at the center of the first light guide 1.

Figure 42:
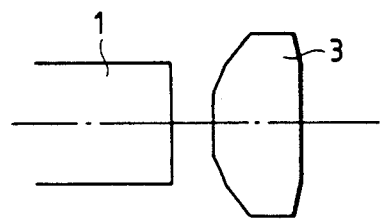

In the lens system shown in FIG. 42, the aspherical surface of the lens component is designed as a surface approximated to a polygonal surface.

Figure 43:
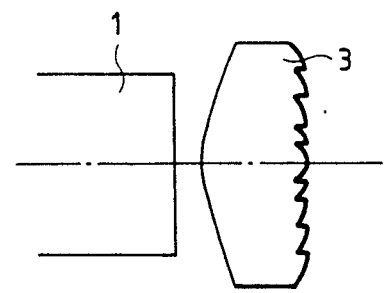

The lens system shown in FIG. 43 consists of a lens component having an aspherical surface similar to the surface of a Fresnel lens.

Figure 44:
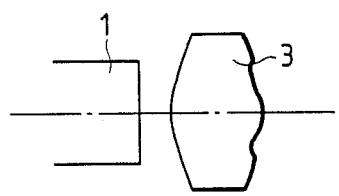

The lens system illustrated in FIG. 44 consists of a lens component having a stepped aspherical surface.

Figure 45:
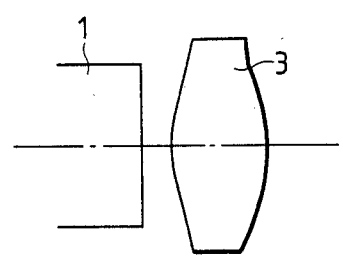

The lens system illustrated in FIG. 45 consists of a lens component having an aspherical surface which is asymmetrical with regard to the optical axis.

Figure 46:
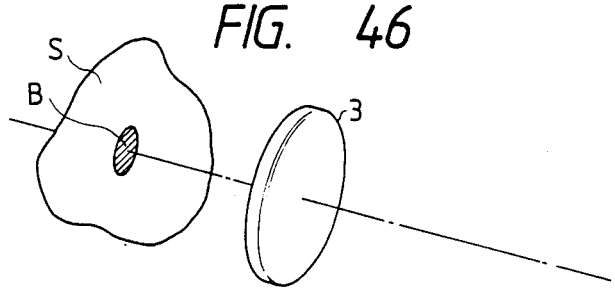

FIG. 46 illustrates an illumination optical system wherein the lens system according to the present invention is so adopted as to illuminate an object directly with the light emitted from a light source S having a certain extent in the direction across the optical axis, and which permits, by covering a portion of the light source located in the vicinity of the optical axis with a shield B, differentiating a ratio in brightness between the center and marginal portion of the visual field from the ratio in the usual illumination optical systems.

Figure 47:
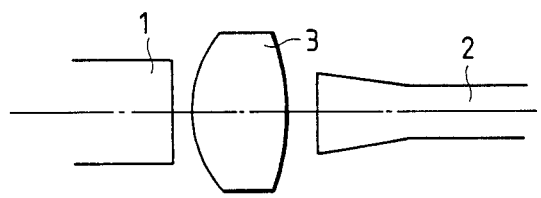

In the illumination optical system illustrated in FIG. 47, the end of incidence of the second light guide 2 is tapered.

Figure 48:
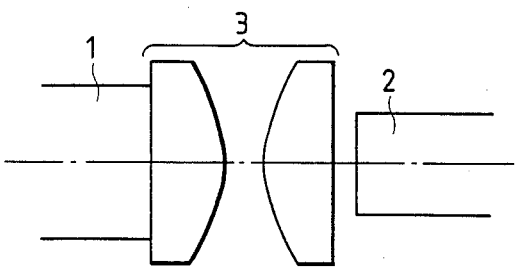
Figure 49:
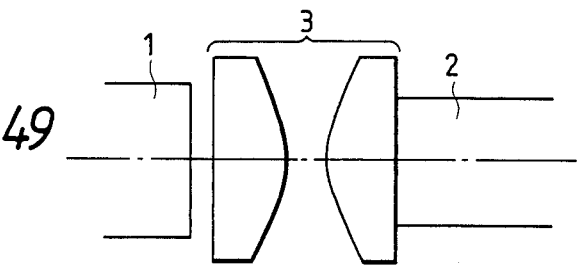
Figure 50:
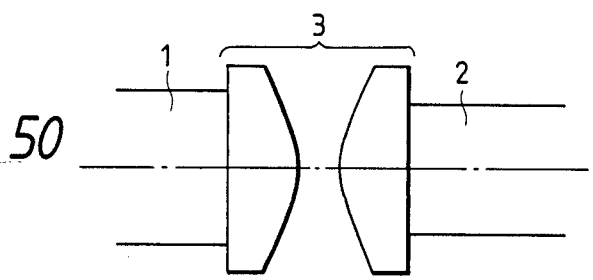

The first light guide 1 is cemented to the lens system in the illumination optical system shown in FIG. 48, the lens system is cemented to the second light guide 2 in the illumination optical system shown in FIG. 49, and the lens system is cemented to both the first light guide 1 and the second light guide 2 in the illumination optical system illustrated in FIG. 50.

Figure 51:
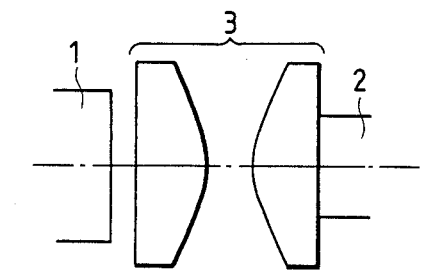

In the illumination optical system illustrated in FIG. 51, the end surface of the second light guide 2 having a defamer smaller than that of the second light guide shown in FIG. 49 is cemented to the lens system for illuminating a surface with the light emerging from the lens component.

Figure 52:
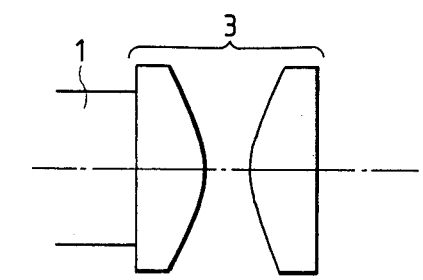

The illumination optical system shown in FIG. 52 is so adapted as to allow the light emitted from a surface-shaped light source to be incident on the second light guide 2.

Figure 53:
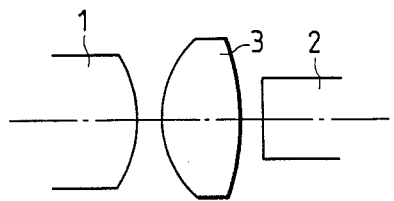

The illumination optical system shown in FIG. 53 comprises a first light guide 1 which has an end surface designed as a spherical surface.

Figure 54:
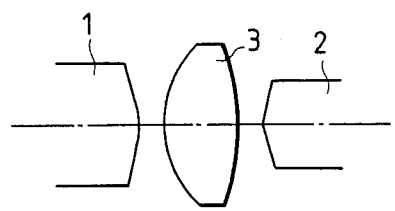

In the illumination optical system shown in FIG. 54, the end surfaces of both the first light guide 1 and the second light guide 2 are designed as conical surfaces.

Figure 55:
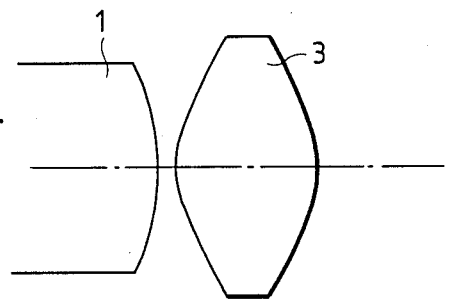

In the illumination optical system illustrated in FIG. 55, the first light guide 1 has a spherical end surface and the lens system is designed as a single aspherical lens component.

Now, description will be made on Embodiments of illumination devices enabling favorable illumination matched with visual fields of observation systems by using the illumination optical system according to the present invention.

Figure 56:
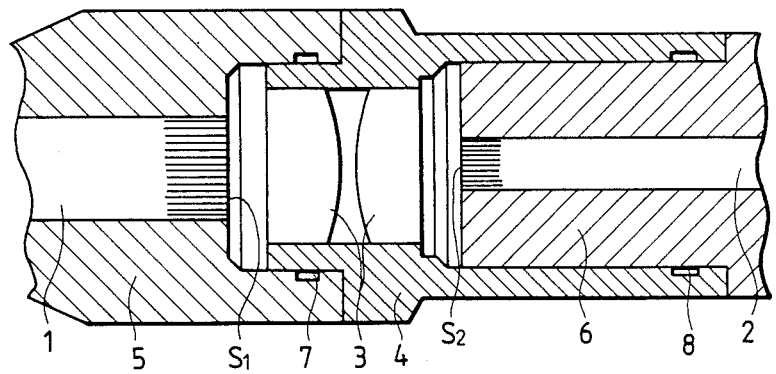
FIGS. 56, 57A, 57B, 58, 59, 60A, 60B, 61, 62 and 63 show sectional views illustrating Embodiments wherein the optical system according to the present invention is used in light guides designed as two blocks.

FIG. 56 shows an illumination device consisting of a first light guide 1, a cap 4 having the lens system 3 mounted thereon and a second light guide 2. The cap 4 is screwed by a thread 8 over the tip mounting frame 6 of the second light guide 2 and by a thread 7 to the tip mounting frame 5 of the first light guide 1 so that the frames and the cap can be disassembled from one another. When these members are assembled as shown in FIG. 56, the end surface of incidence $S_2$ of the second light guide 2 is located in the vicinity of the rear focal point of the lens system 3, and the first light guide 1 is fixed at such a position as to locate the end surface $S_1$ thereof at the position of the front focal point of the lens system 3.

It is sufficient in this Embodiment to use a lens system which has a focal length optimum for the diameter and NA of the first light guide 1 as well as a field angle of the observation system of an endoscope. When the illumination optical system according to the present invention is to be used in combination with endoscopes having different field angles, it is sufficient for practice to prepare the caps 4 equipped with the lens systems 3 having focal lengths matched with the visual fields of the endoscopes and to select one of the lens systems 3 having the focal length optimum for the visual field of the endoscope to be adopted. By taking the measure described above, it is possible to perform illumination at an illumination angles optimum for field angles of the observation systems of endoscopes and with favorable light distribution characteristics.

Figure 57A:
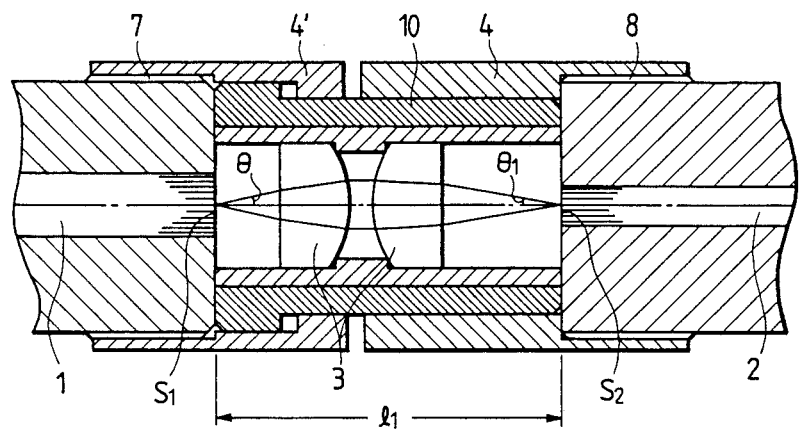
Figure 57B:
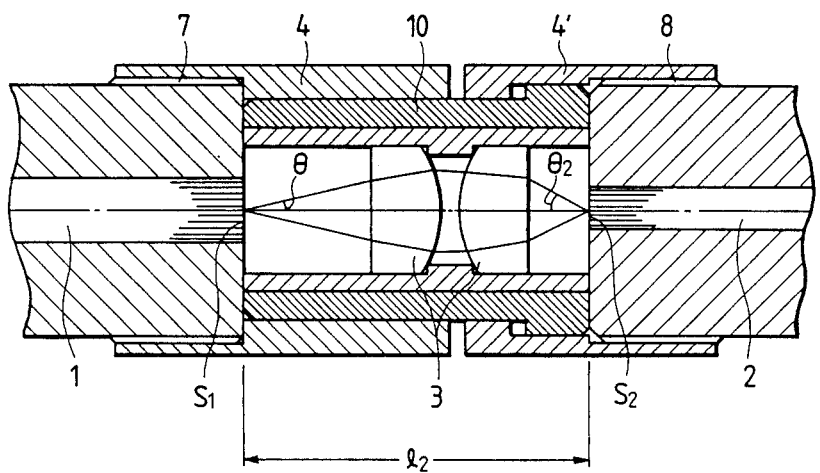

The Embodiment illustrated in FIG. 57A and FIG. 57B is designed as an illumination device wherein the coupling lens system 3 is held in a lens barrel 10, and the caps 4' and 4 having threads formed on the inside surfaces thereof are sequentially fitted and fixed over the lens barrel 10. The first light guide 1 is coupled with the second light guide 2 by way of the lens system 3 as shown in FIG. 57A by screwing the lens barrel having the caps fixed thereto with the tip 5 of the first light guide 1 and the tip 6 of the second light guide 2 respectively. The illumination device is so composed as to locate, in the coupled condition, the end surface of emergence $S_1$ of the first light guide 1 and the end surface of incidence $S_2$ of the second light guide 2 at positions conjugate with each other with regard to the lens system 3.

FIG. 57A shows the illumination device in a condition which is established by detaching the first light guide 1 and the second light guide 2 from the lens system 3, turning the lens barrel 10 horizontally so as to set it in the inverted direction, screwing the tip 5 of the first light guide 1 to the cap 4 and screwing the tip 6 of the second light guide 2 to the cap 4'. When the lens barrel 10 is horizontally turned and set in the position shown in FIG. 57B, the end surface of emergence $S_1$ of the first light guide 1 is located in the vicinity of the front focal point of the lens system 3 and the end surface of incidence $S_2$ of the second light guide 2 is located in the vicinity of the rear focal point of the lens system 3.

Accordingly, magnification of an image formed on 10 the end surface $S_1$ by the lens system 3 and NA are varied between the condition shown in FIG. 57A and that shown in FIG. 57B. That is to say, it is possible to perform illumination optimum for two endoscopes by designing NA in FIG. 57A and NA in FIG. 57B so as to be matched with field angles of the two endoscopes and setting the lens barrel in the inverted direction when the endoscopes are to be replaced with each other.

Further, it is possible in this Embodiment to vary magnification of an image on the end surface of incidence of the second light guide 2 which is transferred from an image on the end surface of emergence of the first light guide 1, and therefore to obtain optimum illumination matched with field angles of endoscopes also by preparing lens barrels 10 containing different lens systems 3 having different distances $l_1$ and $l_2$ between the conjugate points thereof, and replacing the lens barrels in accordance with selection of endoscopes.

Figure 58:
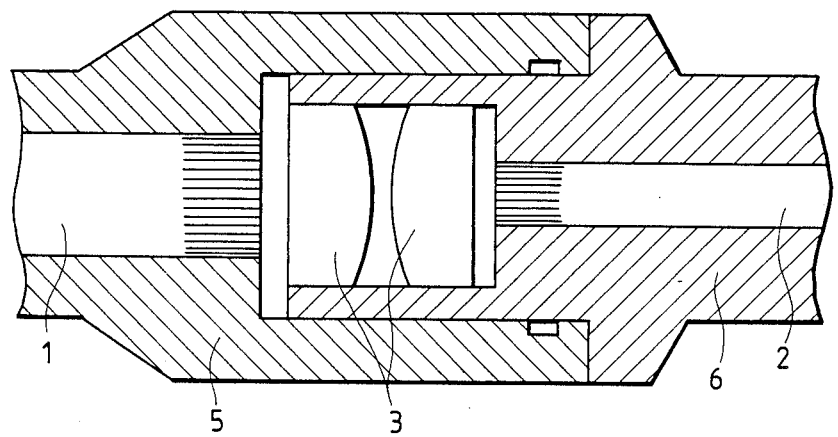

The Embodiment illustrated in FIG. 58 is an illumination optical system wherein the lens system 3 is fixed on the side of the endoscope. Speaking concretely, the lens system 3 is fixed to the tip 6 of the second light guide 2 so as to locate the end surface of incidence $S_2$ of the second light guide 2 in the vicinity of the rear focal point of the lens system 3, and the mounting frame 5 of the first light guide 1 is screwed over the lens system 3.

In this Embodiment wherein the lens system 3 is fixed to the tip 6 of the second light guide 2, lens systems having different focal lengths matched with field angles of endoscopes are to be selectively fixed so as to locate the end surface of incidence of the second light guide 2 in the vicinity of the rear focal points of the lens systems. When the tip 6 containing the lens system 3 is screwed into the tip 5 of the first light guide 1, the end surface of emergence S: of the first light guide 1 is located in the vicinity of the front focal point of the lens system 3.

When the lens systems 3 matched with field angles of observation systems of endoscopes are fixed to the tips of the second light guides, efficient light distribution matched with the field angles of the observation systems can be obtained by coupling the first light guide 1.

Figure 59:
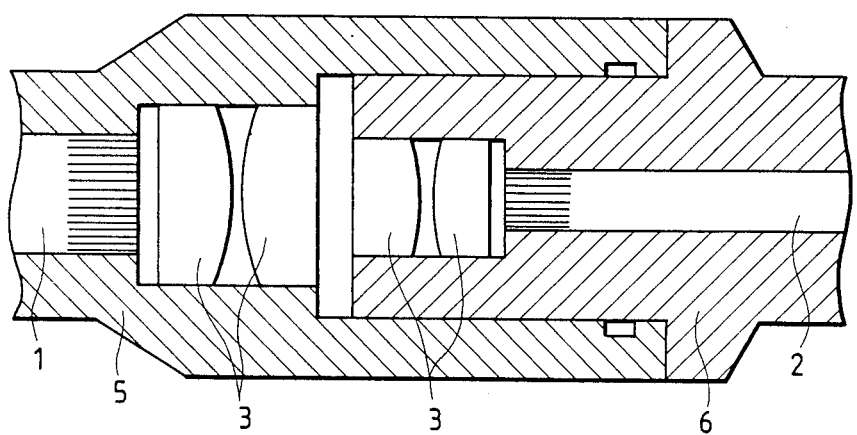

In the Embodiment illustrated in FIG. 59, the lens system consists of a front lens group and a rear lens group, the front lens group is fixed to the tip 5 of the first light guide 1 and the rear lens group is fixed to the tip 6 of the second lens group 2. The tip 5 is screwed over the tip 6. Further, the front lens group and the rear lens group are arranged in an afocal condition. Furthermore, the end surface of emergence $S_1$ of the first light guide 1 and the end surface of incidence $S_2$ of the second light guide 2 are located in the vicinity of the object point and the image point respectively of the lens system 3. When position (distance from the center) of the light emerging from the first light guide 1 is represented by r, position of the light incident on the second light guide is designated by r', NA on the emergence side of the first light guide is denoted by sin $\theta$ and NA on the incidence side of the second light guide is represented by sin $\theta'$, we obtain the following formula (xii):

$$r'/r = \sin\theta/\sin\theta' = \beta \quad \text{(xii)}$$

Further, when focal length of the front lens group is represented by $f_1$ and focal length of the rear lens group is designated by $f_2$, $\theta$ is expressed by the following formula (xiii):

$$\beta = f_2/f_1 \quad \text{(xiii)}$$

On the basis of the formulae (xii) and (xiii), it is possible to design an illumination optical system which can provide light distributions optimum for different field angles of endoscopes by selecting focal lengths of the rear lens group.

Figure 60A:
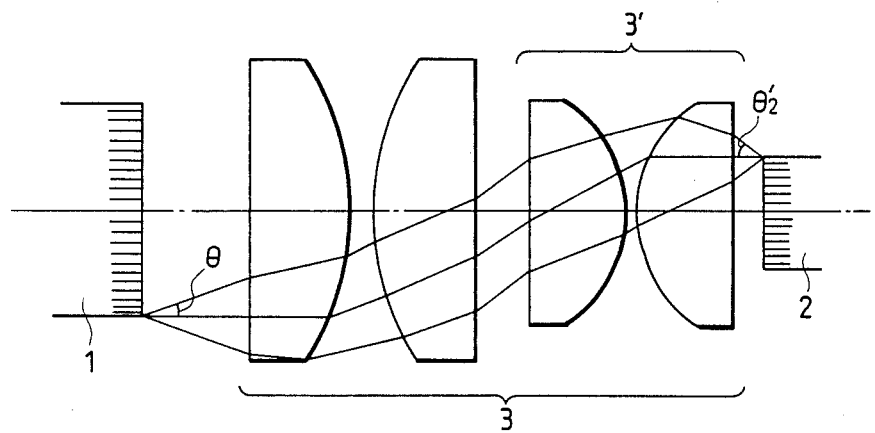
Figure 60B:
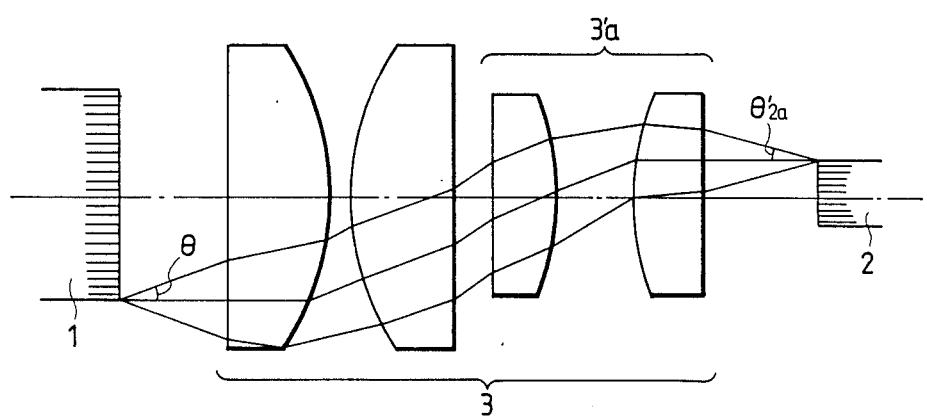

FIG. 60A and FIG. 60B illustrates an illumination optical system which comprises a rear lens group 3' having a focal length $f_2$ in the condition shown in FIG. 60A and another rear lens group 3'a having a different focal length $f_{2a}$ in the condition shown in FIG. 60B. When the illumination optical system uses the rear lens groups 3' and 3a' as shown in these drawings, rays emerging at the same NA are incident at different NA's.

When the illumination field angle of the lens system comprising the rear lens groups 3' having a focal length $f_2$ is represented by $\theta'_2$, and the illumination field angle of the lens system comprising the rear lens group 3'a having a focal length $f_{2a}$ is represented by $\theta'_{2a}$, if $f_2 < f_{2a}$, $\theta'_2 >$. In a case where the rear lens group 3' having the focal length $f_2$ is to be fixed to an endoscope having a field angle of $\omega_2$ and the rear lens group 3'a having the focal length of $f_2$ is to be fixed to another endoscope having a field angle of $\omega_{2a}$, it is possible to compose an illumination optical system providing light distribution optimum for the individual endoscopes by selecting a relation of $\omega_2 > \omega_{2a}$, adjusting adequate values of $f_2$ and $f_{2a}$, and coupling the first light guide comprising the front lens group.

Figure 61:
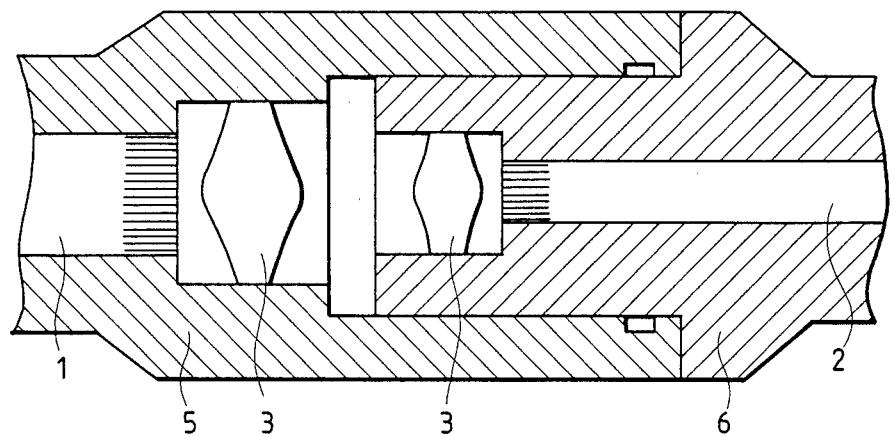

The Embodiment shown in FIG. 61 is a modification example of the illumination optical system illustrated in FIG. 60A and FIG. 60B, and composed of a front lens group and a rear lens group each consisting of a single aspherical lens component.

Figure 62:
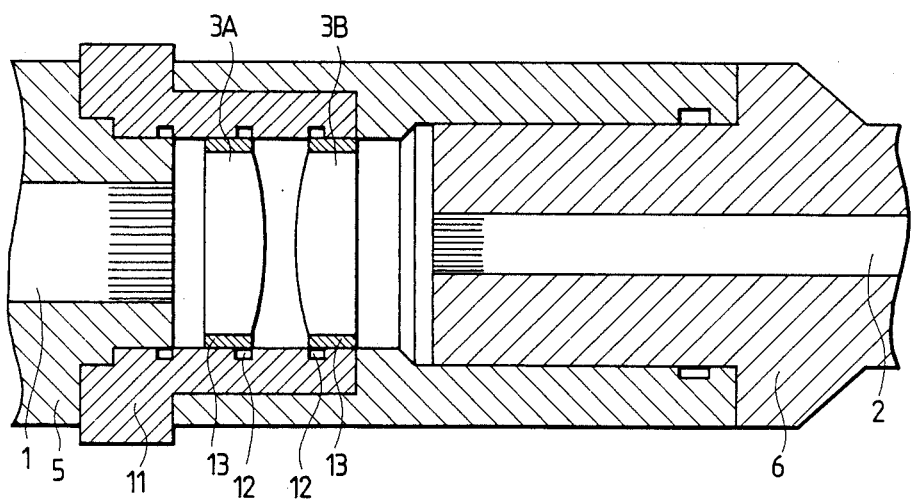

In the Embodiment illustrated in FIG. 62, the lens system is designed as a vari-focal lens system. In this Embodiment, a lens barrel 11 having a cam groove is attached to the first light guide 1, and a lens system 3 consisting of lens components 3A and 3B attached to a frame 13 having a cam pin 12 are arranged in the lens barrel in such a manner that the lens components 3A and B are movable in the direction along the optical axis. The tip 6 of the second light guide 2 is screwed into the lens barrel 11 attached to the first light guide 1.

This Embodiment is so adapted as to perform zooming for varying magnification of the lens system 3 by turning the lens barrel 11 to vary the airspace reserved between the lens components 3A and 3B.

Figure 63:
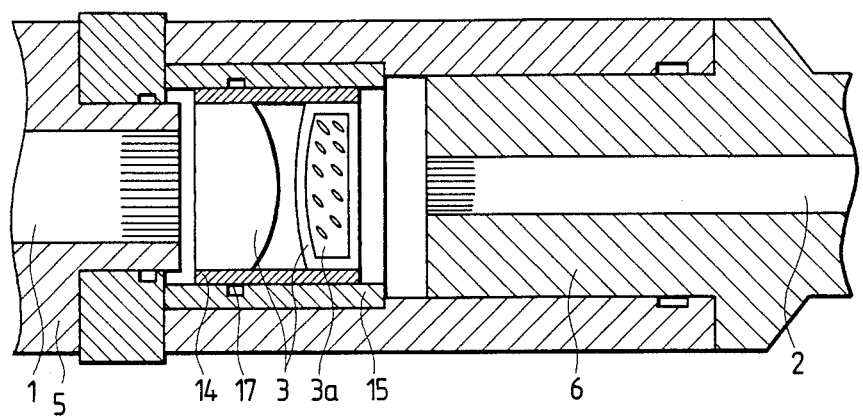

The Embodiment shown in FIG. 63 is an illumination optical system wherein a holding frame 14 which contains a lens system 3 including at least one liquid crystal lens is inserted into a lens barrel 15 attached to the tip 5 of the first light guide 1, and the tip 6 of the second light guide 2 is screwed to the holding frame 14 for coupling.

In the Embodiment shown in FIG. 63, the lens component 3a is designed as a liquid crystal lens and refractive power of the lens system is varied by applying voltage to the liquid crystal of the lens component to change the refractive index thereof. In addition, the lens system is slightly movable as a whole along the optical axis with a cam mechanism so as to locate the end surface of emergence of the first light guide 1 in the vicinity of the front focal point of the lens system and locate the end surface of incidence of the second light guide in the vicinity of the rear focal point of the lens system. Speaking concretely with reference to FIG. 63, the lens system is moved along the cam groove formed in the holding frame 14 by turning the lens barrel 15. As is understood from the foregoing description, the illumination optical system preferred as this Embodiment is so adapted as to permit varying refractive power of the lens system by changing the refractive power of the liquid crystal, and moving the lens system for always the end surface of emergence $S_1$ of the first light guide 1 and the end surface of incidence $S_2$ of the second light guide 2 in the vicinities of the front and rear focal points respectively of the lens system. The illumination optical system can therefore provide optimum illumination by varying refractive power of the lens system in accordance with an endoscope employed.

Figure 64:
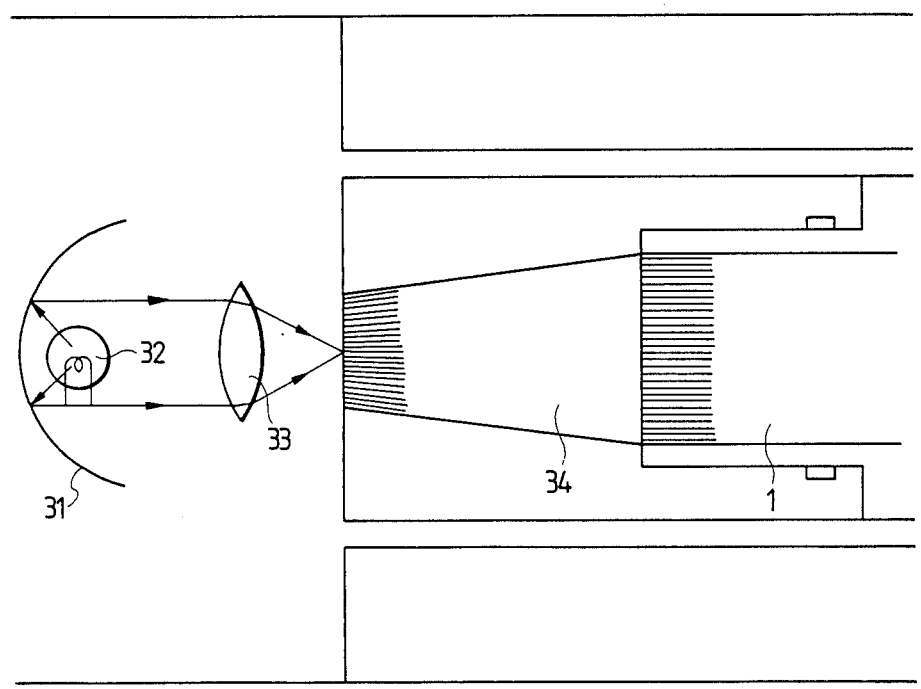
FIG. 64 shows a sectional view illustrating an example of composition of the light source of the illumination device for endoscopes.

FIG. 64 exemplifies an arrangement of the light source and related members in a case where the illumination optical system according to the present invention is to be applied to an instrument using light guides such as an endoscope. In this drawing, the reference numeral 31 represents a reflecting mirror, the reference numeral 32 designates a light source, the reference numeral 33 denotes a condenser lens and the reference numeral 34 a conical fiber bundle. That is to say, the members are arranged in such a manner that the light emitted from the light source 32 is incident on the first light guide 1 through the conical fiber bundle 34.

Adopted as the conical fiber bundle 34 in this arrangement of the light source and related members is an optical fiber bundle having an NA which is equal to or larger than that of the light source. Accordingly, NA of the light incident on the end surface of incidence of the conical fiber bundle 34 is varied during travelling through the conical fiber bundle 34, and NA of the light emerging from the end surface of emergence of the conical fiber bundle 34 is equal to or smaller than that of the first light guide 1. In this arrangement, said conical fiber bundle therefore serves to allow the light to be incident on the first light guide without loss even when NA of the light source is different from that of the first light guide.

We claim:

1. An illumination optical system comprising a surface-shaped light source having a two-dimensional extent across an optical axis, and a positive lens system positioned so as to have its front focal point in the vicinity of the light source, said lens system being adopted to receive light from said light source and to direct the received light toward a surface to be illuminated, the illumination optical system being designed to satisfy a following condition (1) at more than 50% of the sectional area of effective light flux within the range defined by the following condition (2), $$(d\theta/dr_1)/(d\theta/dr_1)_{r_1=0} < f/\sqrt{f^2 - r_1^2} \quad (1)$$

$$0 \leq |r_1| \leq |f| \quad (2)$$

wherein the reference symbol $r_1$ represents distance as measured from the optical axis to an optional point on said surface-shaped light source, the reference symbol $\theta$ designates angle of incidence on a surface to be illuminated formed between the optical axis and the ray emerging from said point in parallel to the optical axis and incident on said illuminated surface, and the reference symbol f denotes focal length of said lens system.

2. An illumination optical system according to claim 1, satisfying said conditions (1) and (2) within a range of 10 to 15 when angle of divergence of the light flux emitted from said light source and incident on the lens system is represented by $\phi$.

3. An illumination optical system according to claim 2, wherein said surface-shaped light source is an end surface of emergence of a first light guide.

4. An illumination optical system according to claim 3, wherein said surface to be illuminated is an end surface of incidence of a second light guide.

5. An illumination optical system according to claim 3, wherein a black portion is arranged at a center of said first light guide.

6. An illumination optical system according to claim 1, 2, 3 or 4 wherein said positive lens system comprises at least one positive lens component and, when the direction along the optical axis is taken as the x axis and the direction perpendicular to the optical axis is taken as the y axis, said positive lens component has an aspherical surface approximated by the following formula (3) and satisfies the following conditions (4) through (6) at least at 50% of the sectional area of the effective light flux:

$$x = \frac{y^2/R}{1 + \sqrt{1 - P(y/R)^2}} + Ey^4 + Fy^6 + Gy^8 + \ldots \quad (3)$$

-continued $$0.2 \leq D/f \leq 3 \quad (4)$$

$$P < 0 \quad (5)$$

$$|\Delta| \leq |x_{max}|/2 \quad (6)$$

wherein the reference symbol P represents conic constant, the reference symbols E, F and G represents the coefficients of aspherical surface, of the fourth, sixth, eighth, ... orders, respectively, the reference symbol R designates radius of curvature of said aspherical surface on the optical axis, the reference symbol D denotes distance as measured from the optical axis to the outermost marginal portion of said surface-shaped light source, the reference symbol $\Delta$ represents deviation between said aspherical surface expressed by the formula (3) and the actual aspherical surface, and the reference symbol $X_{max}$ designates the maximum value of $|x|$ expressed by the formula (3) in effective diameter of said lens component.

7. An illumination optical system according to claim 1, 2, 3 or 4 wherein the optical axis of the lens system is inclined relative to the optical axis of the illumination optical system.

8. An illumination optical system according to claim 1, 2, 3 or 4 wherein the lens system consists of a lens component having a clad layer formed on the circumferential edge thereof.

9. An illumination optical system according to claim 1, 2, 3 or 4, wherein the aspherical surface in said positive lens component is approximated to a polyhedron.

10. An illumination optical system according to claim 1, 2, 3 or 4, wherein the aspherical surface is designed as a Fresnel surface.

11. An illumination optical system according to claim 1, 2, 3 or 4, wherein the aspherical surface is designed as a discontinuous aspherical surface.

12. An illumination optical system according to claim 1, 2, 3 or 4, wherein the apsherical surface is designed as an aspherical surface asymmetrical with regard to the optical axis.

13. An illumination optical system for endoscopes according to claim 3 or 4, wherein said second light guide is arranged in each of a plural number of endoscopes equipped with observation systems having different field angles, said lens system and said first light guide being connected to each other, said lens system is attachable and detachable to and from said second light guide, and said lens system is replaceable or has variable focal length.

14. An illumination optical system according to claim 1, 2, 3 or 4, wherein the surface to be illuminated is positioned in the vicinity of the rear focal point of said positive lens system.

15. An illumination optical system according to claim 3, 4 or 5, wherein the end surface of emergence of said first light guide is positioned in the vicinity of the front focal point of said positive lens system.

16. An illumination optical system according to claim 1 wherein said positive lens system comprises at least one positive lens component and, when the direction along the optical axis is taken as the x axis and the direction perpendicular to the optical axis is taken as the y axis, said positive lens component has an aspherical surface approximated by the formula (3) and satisfies the conditions (4), (6), (7), (8), (9), (10) and (11) at least at 50% of the area through which the effective light flux passes:

$$x = \frac{y^2/R}{1 + \sqrt{1 - P(y/R)^2}} + Ey^4 + Fy^6 + Gy^8 + \ldots \quad (3)$$

$$0.2 \leq D/f \leq 3 \quad (4)$$

$$|\Delta| \leq |x_{max}|/2 \quad (6)$$

$$0 \leq P < 1 \quad (7)$$

$$E \leq 0 \quad (8)$$

$$F \geq 0 \quad (9)$$

$$0 \leq |E \cdot D^{-3}| \leq 1 \quad (10)$$

$$0 \leq |F \cdot D^{-3}| \leq 0.5 \quad (11)$$

wherein the reference symbol P represents conic constant, the reference symbols E, F and G represents the coefficients of aspherical surface, of the fourth, sixth, eighth, ... orders, respectively, the reference symbol R designates radius of curvature of said aspherical surface on the optical axis, the reference symbol D denotes distance as measured from the optical axis to the outermost marginal portion of said surface-shaped light source, the reference symbol Δ represents deviation between said aspherical surface expressed by the formula (3) and the actual aspherical surface, and the reference symbol $x_{max}$ designates the maximum value of $|x|$ expressed by the formula (3) in effective diameter of said lens component.

17. An illumination optical system according to claim 1 wherein said positive lens system comprises at least one positive lens component and, when the direction along the optical axis is taken as the x axis and the direction perpendicular to the optical axis is taken as the y axis, said positive lens component has an aspherical surface approximated by the following formula (3) and satisfies the following conditions (4), (6), (8), (9), (12), (13) and (14):

$$x = \frac{y^2/R}{1 + \sqrt{1 - P(y/R)^2}} + Ey^4 + Fy^6 + Gy^8 + \ldots \quad (3)$$

$$0.2 \leq D/f \leq 3 \quad (4)$$

$$|\Delta| \leq |x_{max}|/2 \quad (6)$$

$$E \leq 0 \quad (8)$$

$$F \geq 0 \quad (9)$$

$$P \geq 1 \quad (12)$$

$$0.1 \leq |E \cdot D^{-3}| \leq 0.6 \quad (13)$$

$$0 \leq |F \cdot D^{-3}| \leq 0.1 \quad (14)$$

wherein the reference symbol P represents conic constant, the reference symbols E, F and G represents the coefficients of aspherical surface, of the fourth, sixth, eighth, ... orders, respectively, the reference symbol R designates radius of curvature of said aspherical surface on the optical axis, the reference symbol D denotes distance as measured from the optical axis to the outermost marginal portion of said surface-shaped light source, the reference symbol Δ represents deviation between said aspherical surface expressed by the formula (3) and the actual aspherical surface, and the reference symbol $x_{max}$ designates an maximum value of $|x|$ expressed by the formula (3) in effective diameter of said lens component.

18. An illumination optical system according to claim 6 wherein said lens system comprises a plural number of aspherical surfaces and satisfies the following conditions (15) and (16):

$$P_1/P_2 \leq 2$$

$$|\omega_1(D)/\omega_2(D)| \geq 0.5$$

wherein the reference symbol $P_1$ represents the conic constant for the aspherical surface formed on a surface facing said surface-shaped light source, the reference symbol $P_2$ designates conic constant for the aspherical surface facing said surface to be illuminated, the reference symbols ω, (D) denotes inclination angle of the surface located on said surface-shaped light source relative to the y axis at a point located at a distance of D from the optical axis and the reference symbol ω, (D) represents inclination angle of the surface located on said surface to be illuminated relative to the y axis at a point of located at a distance from D from the optical axis.

19. An illumination optical system according to claim 1 wherein the optical axis of the lens system is shifted from the optical axis of the illumination optical system.

20. An illumination optical system according to claim 8, wherein the boundary between said clad layer and the lens component is inclined to the optical axis.

21. An illumination optical system according to claim 6, wherein a clad layer is formed on the circumferential edge of the lens component.

22. An illumination optical system according to claim 3, wherein a single fiber is arranged between the end surface of emergence of the first light guide and the lens system.

23. An illumination optical system according to claim 6, wherein a single fiber is arranged between the lens system and the end surface of incidence of the second light guide.

24. An illumination optical system according to claim 4, wherein said first light guide and said lens system are cemented to each other.

25. An illumination optical system according to claim 4 or 24, comprising a second light guide having an end surface of incidence located in the vicinity of the rear focal point of said lens system, said lens system and said second light guide being connected to each other.

26. An illumination optical system according to claim 4, wherein the end surface of emergence of said first light guide or the end surface of incidence of said second light guide is designed as a curved surface.

27. An illumination optical system for endoscopes according to claim 13, wherein said lens system and said second light guide are arranged in said endoscopes.

28. An illumination optical system according to claim 15, wherein the end surface of incidence of said second light guide is positioned in the vicinity of the rear focal point of said positive lens system.

29. An illumination optical system according to claim 16 wherein said lens system comprises a plural number of aspherical surfaces and satisfies the following conditions (15) and (16):

$$P_1/P_2 \leq 2 \quad (15)$$

$$|\omega_1(D)/\omega_2(D)| \geq 0.5 \tag{16}$$

wherein the reference symbol $P_1$ represents the conic constant for the aspherical surface formed on a surface facing said surface-shaped light source, the reference symbol $P_2$ designates conic constant for the aspherical surface facing said surface to be illuminated, the reference symbols $\omega$, (D) denotes inclination angle of the surface located on said surface-shaped light source relative to the y axis at a point located at a distance of D from the optical axis and the reference symbol $\omega$ (D) represents inclination angle of the surface located on said surface to be illuminated relative to the y axis at a point of located at a distance of D from the optical axis.

30. An illumination optical system according to claim 17, wherein said lens system comprises a plural number of aspherical surfaces and satisfies the following conditions (15) and (16):

$$P_1/P_2 \leq 2 \tag{15}$$

$$|\omega(D)/\omega_2(D)| \geq 0.5 \tag{16}$$

wherein the reference symbol $P_1$ represents the conic constant for the aspherical surface formed on a surface facing said surface-shaped light source, the reference symbol $P_2$, designates conic constant for the aspherical surface facing said surface to be illuminated, the reference symbol $\omega$, (D) denotes inclination angle of the surface located on said surface-shaped light source relative to the y axis at a point located at a distance of D from the optical axis and the reference symbol $\omega$, (D) represents inclination angle of the surface located on said surface to be illuminated relative to the y axis at a point of located at a distance of D from the optical axis.

31. An illuminated optical system according to claim 16, wherein a clad layer is formed on the circumference edge of the lens component.

32. An illumination optical system according to claim 17, wherein a clad layer is formed on the circumferential edge of the lens component.

33. An illumination optical system according to claim 16, wherein a single fiber is arranged between the surface-shaped light source and the lens system.

34. An illumination optical system according to claim 32, wherein a single fiber is arranged between the surface-shaped light source and the lens system.

35. An illumination optical system according to claim 33, wherein a single fiber is arranged between the lens system and the surface to be illuminated.

36. An illumination optical system according to claim 34, wherein a single fiber is arranged between the lens system and the surface to be illuminated.

37. An illumination optical system for endoscopes comprising:
   a light source,
   a first light guide for receiving light from said light source on an end surface of incidence thereof and transmitting the light to an end surface of emergence thereof,
   a lens system having positive refractive power and arranged after the end surface of emergence of said first light guide, and
   any one of endoscopes equipped with observation optical systems having field angles different from one another and second light guides,
   and adapted in such a manner:
   that the second light guide of said one of endoscopes is arranged attachably and detachably to and from said lens system having positive refractive power, that at least one of the lens components constituting said lens system is replaceable with regard to said first light guide or movable along the optical axis, and the said at least one of the lens components of the lens system is replaced or moved, when the second light guide of said one of endoscopes is detached and the second light guide of another endoscope is attached, in such a manner that the end surface of emergence of said first light guide and the end surface of incidence of the second light guide of said another endoscope are set in a positional relationship conjugate with each other with regard to said lens system.

38. An illumination optical system for endoscopes according to claim 37, wherein said second light guides and said lens systems are arranged in said endoscopes.

* * * * *